(12) United States Patent
Laham et al.

(10) Patent No.: US 9,259,318 B2
(45) Date of Patent: Feb. 16, 2016

(54) PERICARDIAL REINFORCEMENT DEVICE

(75) Inventors: Roger J. Laham, Brookline, MA (US); Graham Stewart Gardner, Sudbury, MA (US); Thomas William Hulme, London (GB); Joanna J. Wykrzykowska, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1544 days.

(21) Appl. No.: 11/788,366

(22) Filed: Apr. 19, 2007

(65) Prior Publication Data

US 2008/0021266 A1 Jan. 24, 2008

Related U.S. Application Data

(60) Provisional application No. 60/793,085, filed on Apr. 19, 2006.

(51) Int. Cl.
*A61F 2/02* (2006.01)
*A61F 2/24* (2006.01)

(52) U.S. Cl.
CPC ....... *A61F 2/2481* (2013.01); *A61F 2002/2484* (2013.01)

(58) Field of Classification Search
CPC ........ A61B 17/00; A61B 17/32; A61B 19/00; A61F 2/02; A61F 13/00; A61H 31/00; A61M 1/12
USPC ....................... 600/16, 37; 601/153; 623/3.16
See application file for complete search history.

(56) References Cited

U.S. PATENT DOCUMENTS

| | | | |
|---|---|---|---|
| 5,702,343 A | 12/1997 | Alferness | |
| 5,707,336 A * | 1/1998 | Rubin | ............................. 600/17 |
| 5,800,528 A | 9/1998 | Lederman et al. | |
| 6,077,218 A | 6/2000 | Alferness | |
| 6,165,122 A | 12/2000 | Alferness | |
| 6,293,906 B1 | 9/2001 | Vanden Hock et al. | |
| 6,375,608 B1 | 4/2002 | Alferness | |
| 6,416,459 B1 | 7/2002 | Haindl | |
| 6,425,856 B1 | 7/2002 | Shapland et al. | |
| 6,432,039 B1 | 8/2002 | Wardle | |
| 6,482,146 B1 | 11/2002 | Alferness et al. | |
| 6,544,168 B2 | 4/2003 | Alferness | |
| 6,579,226 B2 | 6/2003 | Vanden Hock et al. | |
| 6,626,821 B1 | 9/2003 | Kung et al. | |
| 6,645,139 B2 | 11/2003 | Haindl | |
| 6,682,476 B2 | 1/2004 | Alferness et al. | |
| 6,689,048 B2 | 2/2004 | Vanden Hock et al. | |
| 6,846,296 B1 | 1/2005 | Milbocker et al. | |
| 6,881,185 B2 | 4/2005 | Vanden Hock et al. | |
| 6,902,524 B2 | 6/2005 | Alferness et al. | |

(Continued)

FOREIGN PATENT DOCUMENTS

FR 2645739 10/1990
WO WO 03/061455 7/2003

*Primary Examiner* — Christine H Matthews
(74) *Attorney, Agent, or Firm* — McCarter & English, LLP

(57) ABSTRACT

The following relates to catheter-based devices, systems, and methods for minimally-invasively delivering an inflatable pericardial support into the pericardial space of a mammalian myocardium. The devices and systems include extending and positioning plural support members through a catheter into the pericardial space and then positioning the inflatable member on the epicardial surface of the myocardium. Once positioned, fluid can be delivered to the inflatable member to provide a confining pressure to the myocardium.

47 Claims, 26 Drawing Sheets

(56) References Cited

U.S. PATENT DOCUMENTS

| | | | |
|---|---|---|---|
| 2001/0041821 A1* | 11/2001 | Wilk | ............................ 600/16 |
| 2003/0004396 A1 | 1/2003 | Vanden Hock et al. | |
| 2003/0060895 A1 | 3/2003 | French et al. | |
| 2003/0149333 A1 | 8/2003 | Alferness | |
| 2004/0102678 A1 | 5/2004 | Haindl | |
| 2004/0133069 A1 | 7/2004 | Shapland et al. | |
| 2004/0138521 A1 | 7/2004 | Grabek et al. | |
| 2004/0181124 A1 | 9/2004 | Alferness | |
| 2004/0230091 A1 | 11/2004 | Lau et al. | |
| 2005/0059854 A1 | 3/2005 | Hock et al. | |
| 2005/0192474 A1 | 9/2005 | Vanden Hock et al. | |
| 2005/0197527 A1 | 9/2005 | Bolling | |
| 2005/0197528 A1 | 9/2005 | Vanden Hock et al. | |
| 2005/0228217 A1 | 10/2005 | Alferness et al. | |
| 2005/0256368 A1 | 11/2005 | Klenk et al. | |
| 2005/0272969 A1 | 12/2005 | Alferness et al. | |
| 2006/0009676 A1 | 1/2006 | Melvin | |

* cited by examiner

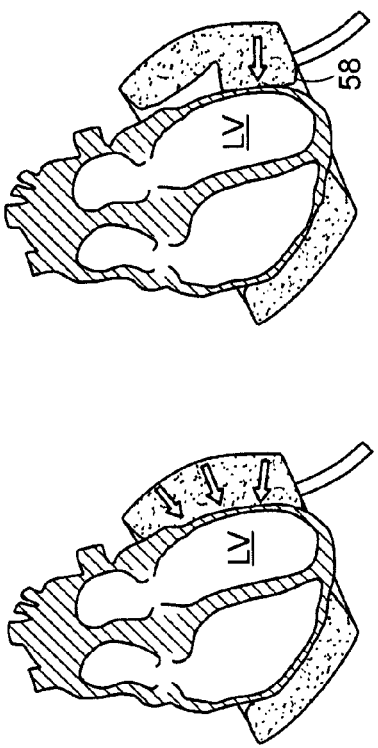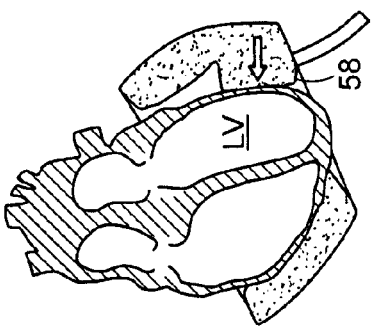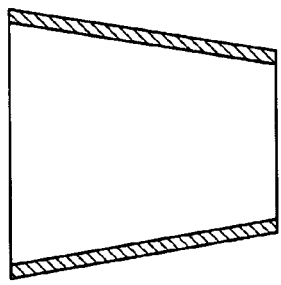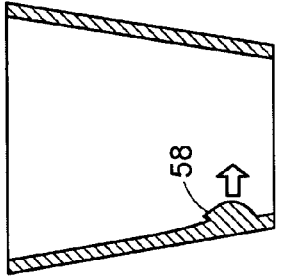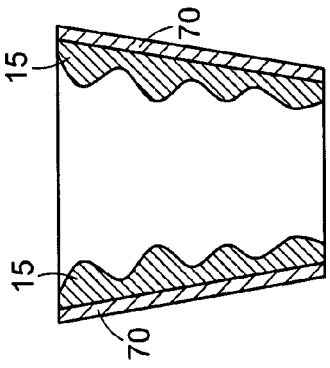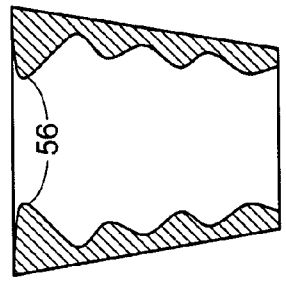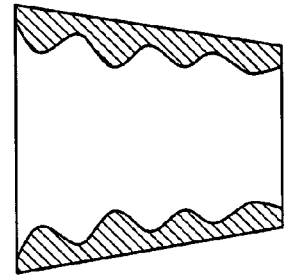

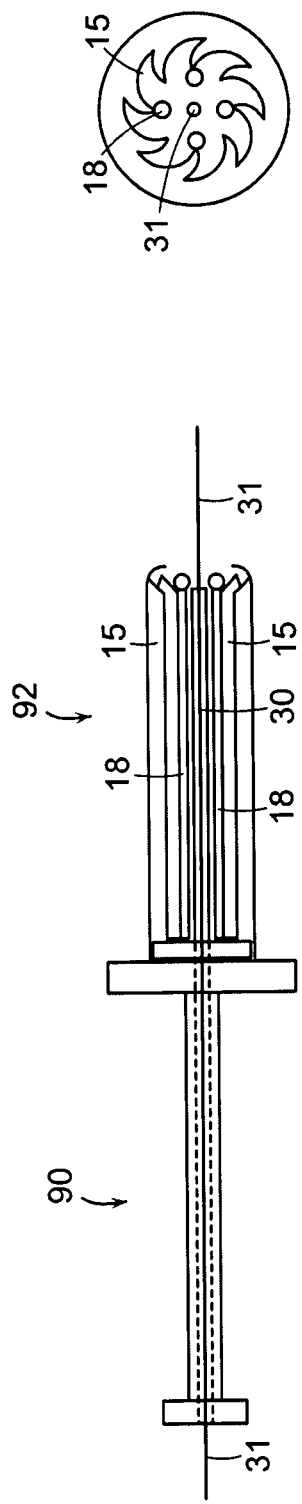
FIG. 11B
FIG. 11A
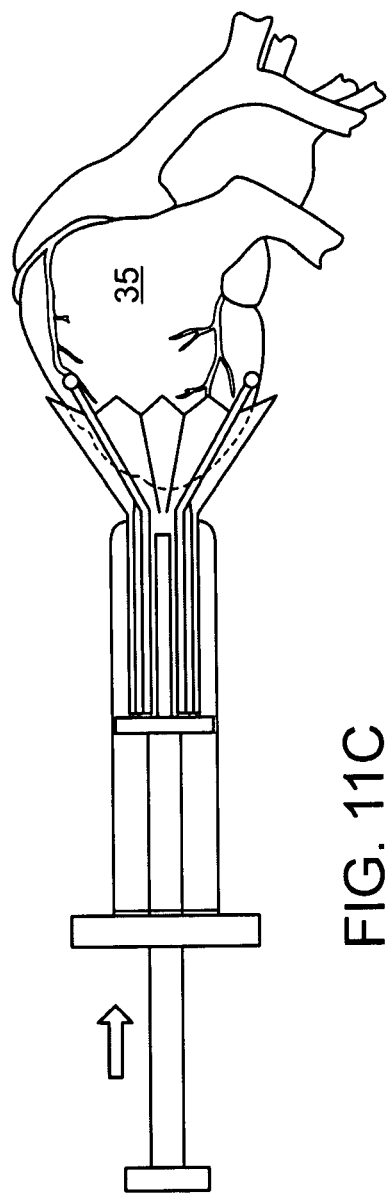
FIG. 11C

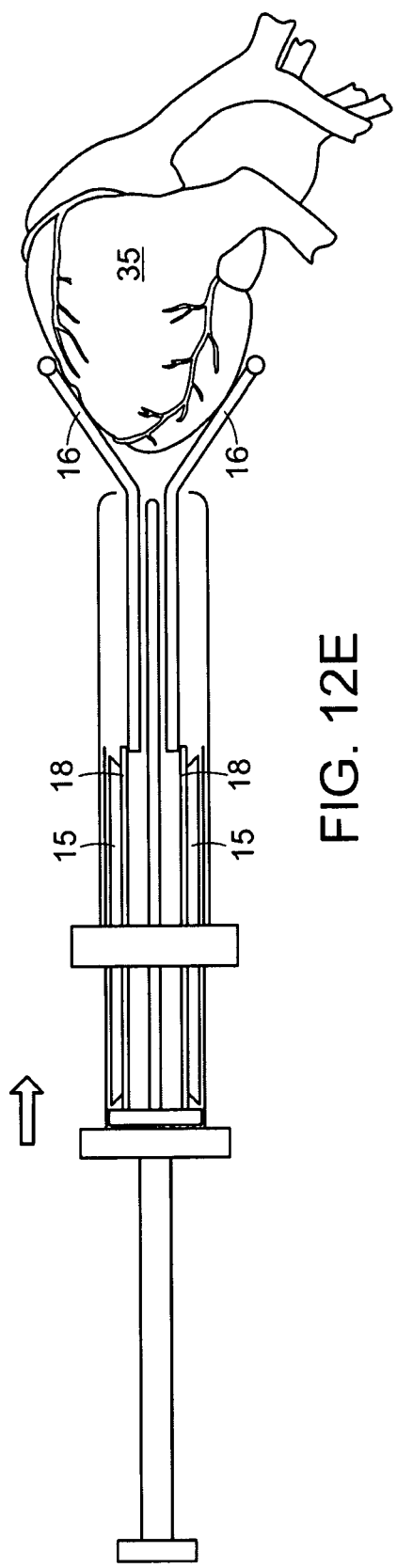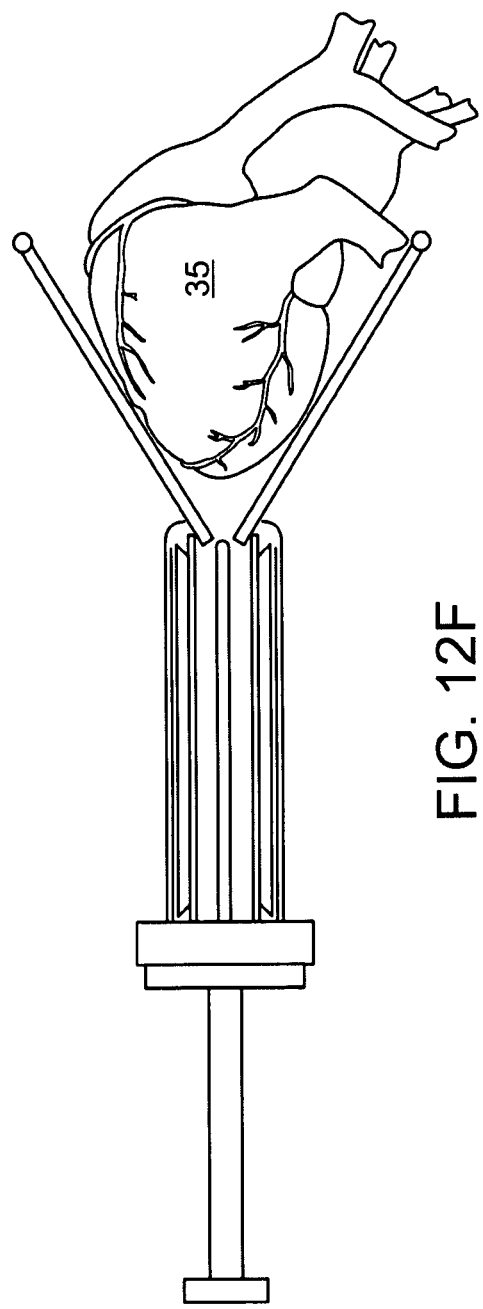
FIG. 12E
FIG. 12F

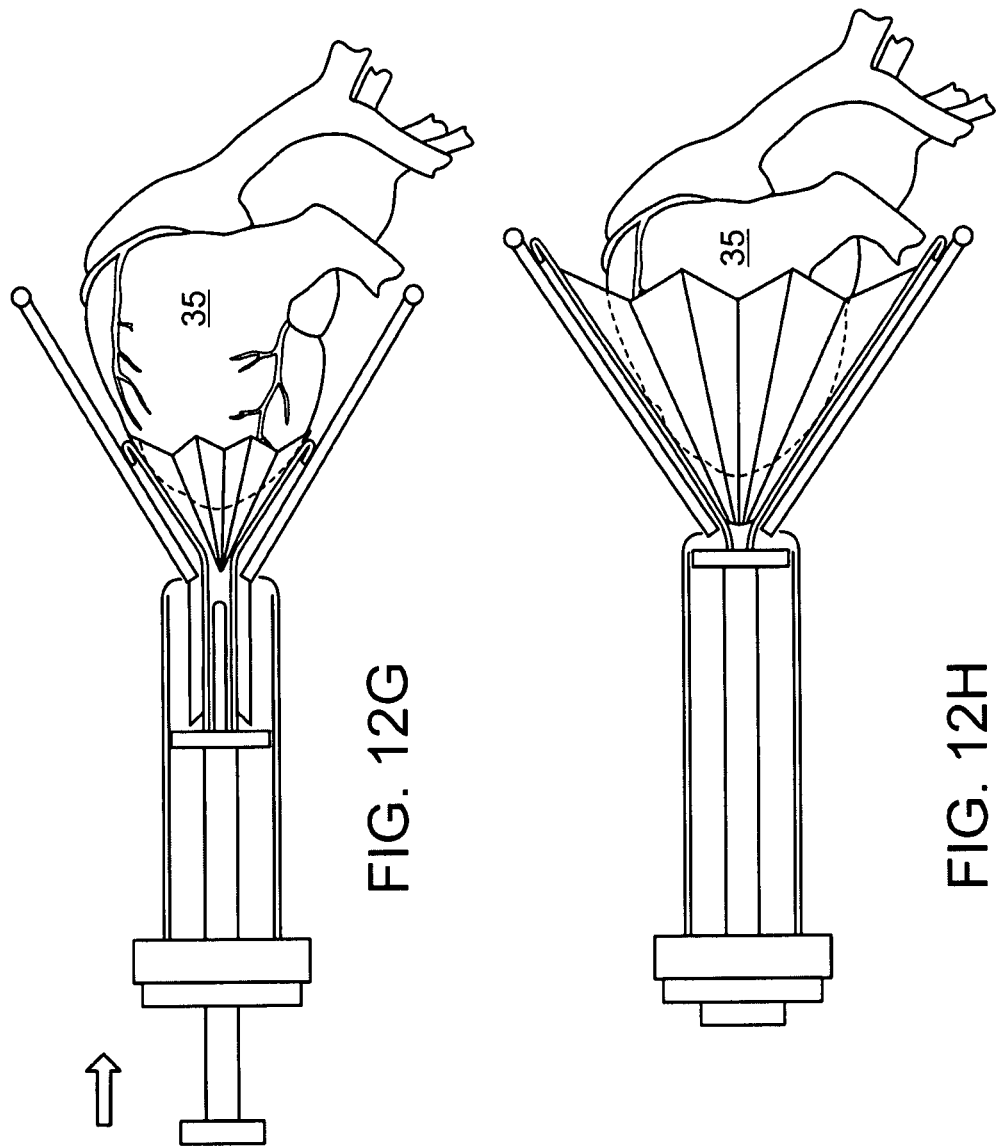

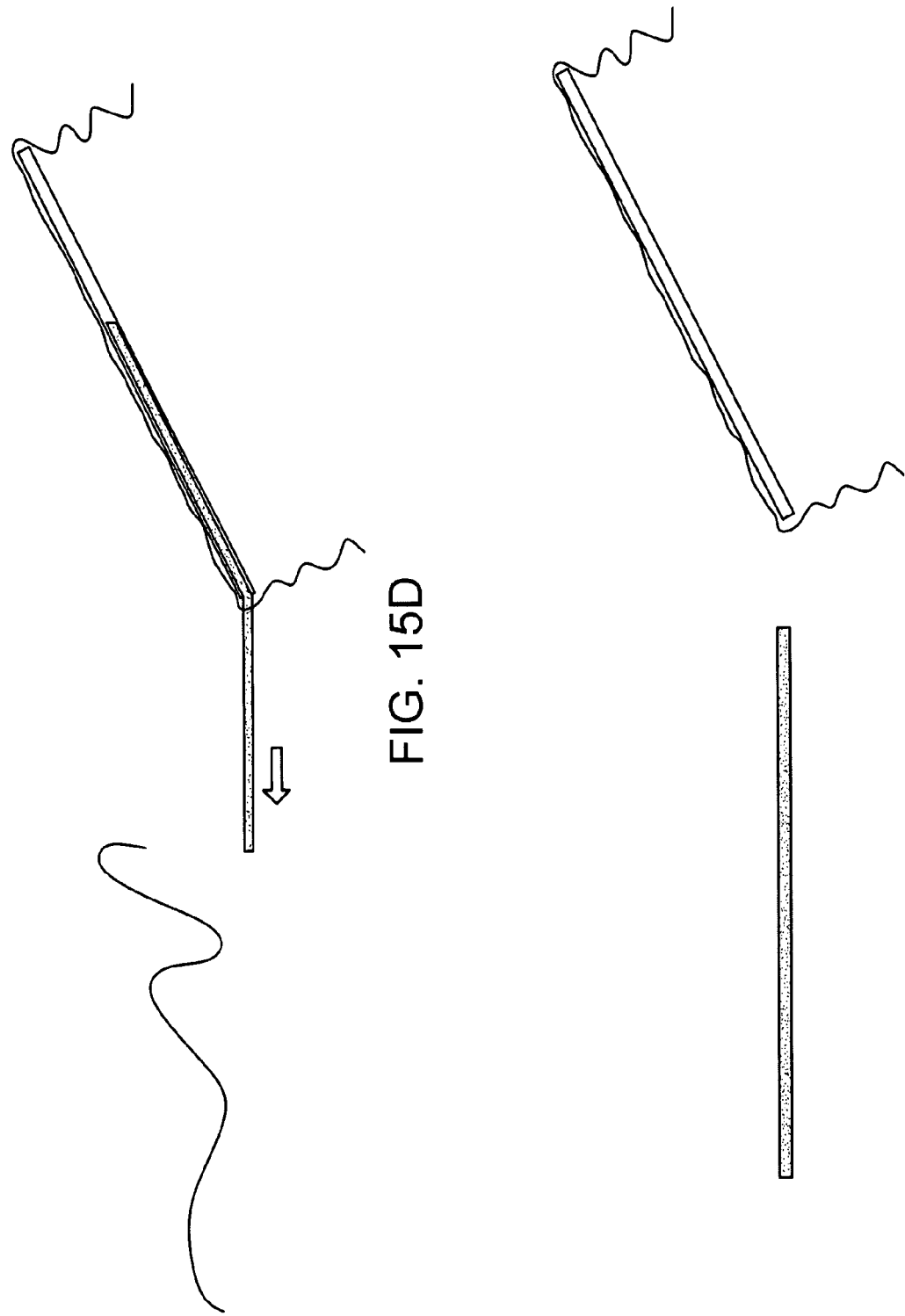

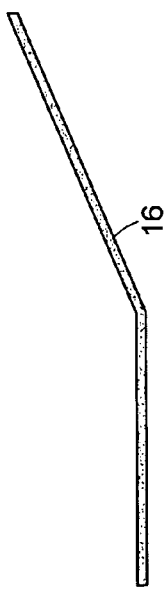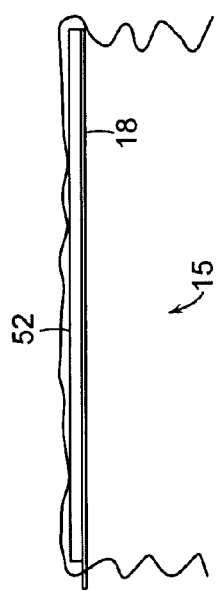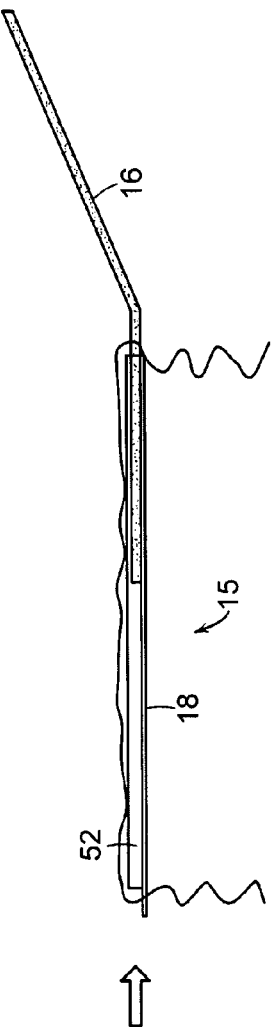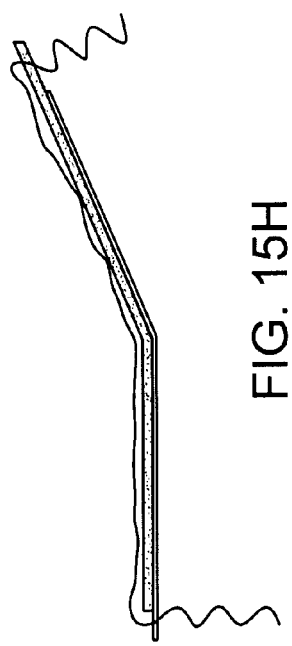
FIG. 15F
FIG. 15G
FIG. 15H

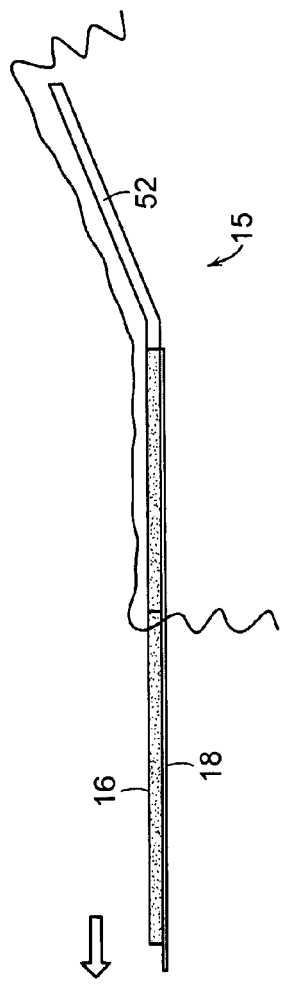
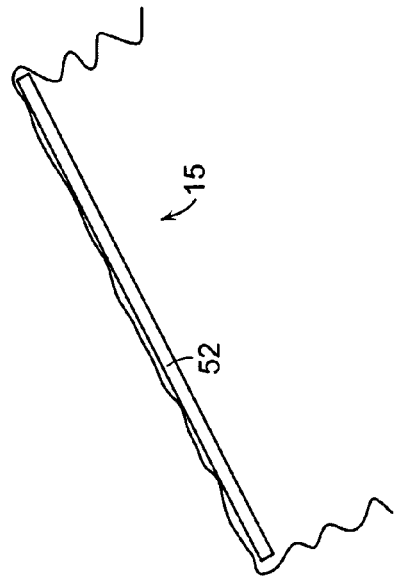
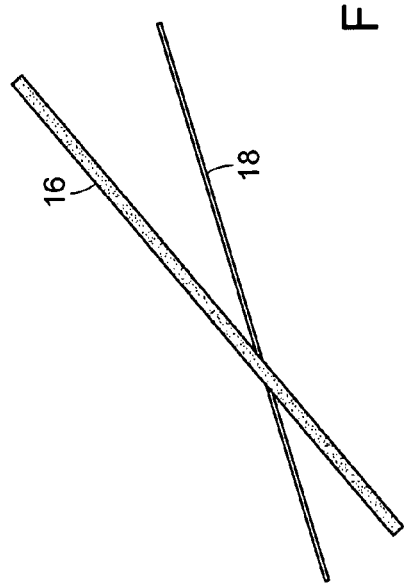
FIG. 15I
FIG. 15J

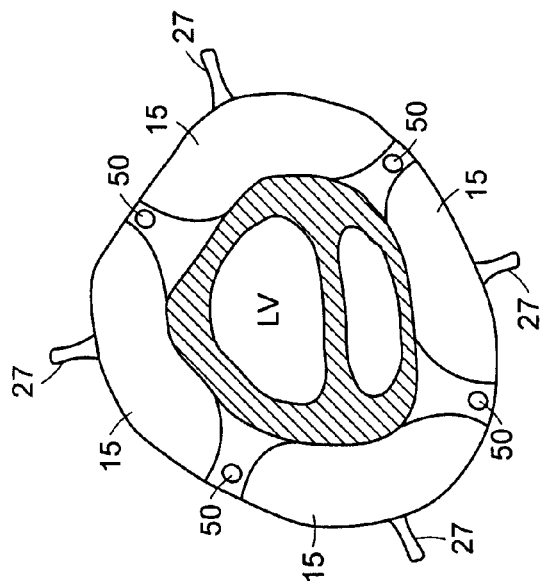
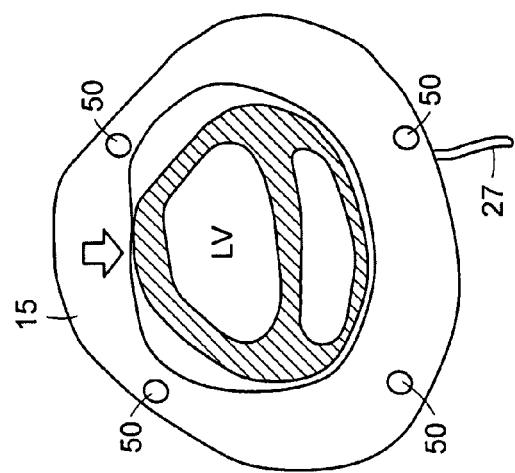
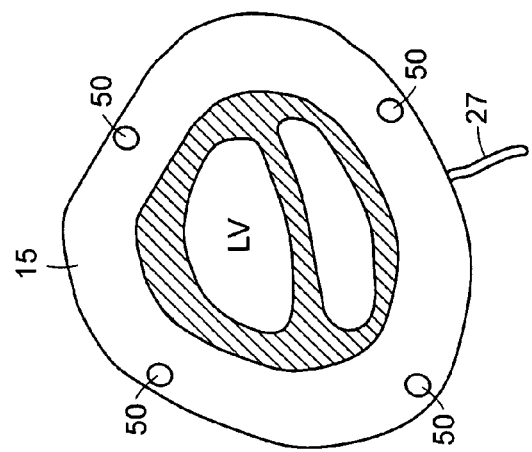

PERICARDIAL REINFORCEMENT DEVICE

CROSS REFERENCE TO RELATED APPLICATION

This application claims the priority of U.S. Provisional Application No. 60/793,085 filed Apr. 19, 2006 and entitled, PERICARDIAL REINFORCEMENT DEVICE. The provisional application is hereby incorporated by reference in its entirety.

BACKGROUND OF THE INVENTION

1. Field of the Invention

The present invention relates to devices, systems, and methods for delivering a pericardial reinforcement device onto the epicardium of a mammalian myocardium, more particularly, to devices, systems, and methods for minimally-invasively delivering an inflatable pericardial "sail" into the pericardial space for attachment to the myocardium.

2. Background

For many patients suffering from, e.g., cardiomyopathy, progressive dilation of the left ventricle of the cardial muscle, i.e., the heart, can precede an end-stage disease. Dilation renders the heart less efficient as it struggles to maintain contractile function. Moreover, the mechanical burden of adverse remodeling is thought to increase wall stress and, further, to impair cardiac function. This is particularly problematic when dealing with the left ventricle, which is the heart's pump.

The medical world has sought with some success to treat cardial dilation with medication. However, many of the medications include undesirable side effects. As a result, medications do not offer a long-term solution for all patients.

In recent years, those skilled in the art have sought mechanical means to prevent or constrict dilation. For example, the CorCap Cardiac Support Device™ manufactured by Acorn Cardiovascular, Inc. of Minnetonka, Minn. was the subject of a study published in December 2004. The study reported the results of 48 patients who, as part of open-heart surgery, underwent an invasive implantation of a restrictive, mesh-like device, which was wrapped around the patients' hearts to slow left ventricle dilation. The findings of the study suggest that, by applying a restrictive mechanical force around the heart, adverse left ventricle remodeling in patients with cardiomyoplasty can be stabilized and, possibly, can be reversed. One shortcoming of the CorCap and similar devices is the invasive nature of the procedure.

Therefore, it would be desirable to provide alternative minimally invasive, systems that will reduce risk and improve recovery time.

SUMMARY OF THE INVENTION

The present invention discloses a minimally-invasive cardiac treatment device. The device includes support elements that are positionable in the pericardial space about a mammalian myocardium and an inflatable member that is coupled to and movable along the support elements from a first position to a deployed position.

In a preferred embodiment of the invention, the support element includes an actuator such as a pulley or spindle section with which all actuating mechanism can be used to position the inflatable member. The device can also include a slotted portion through which the inflatable member can travel.

The device further includes a fluid infusion port for filling the inflatable member with a fluid and/or a pouch for adjusting fluid pressure in the inflatable member.

A minimally-invasive system for cardiac treatment is also disclosed. The system includes a catheter for entering a mammalian pericardium; a plurality of support members (or "masts") that are extendable from the lumen of the catheter into pericardial space about the myocardium; and an inflatable member (or "sail") coupled to and movable along the support members.

The system further includes a rod or tube member for advancing the inflatable member through the catheter and for positioning the member between adjacent support members, a detaching mechanism that detaches the support member from the rod, a filling tube for filling the inflatable member with a fluid, and/or a pouch for adjusting fluid pressure in the inflatable member after the detaching mechanism has detached the plurality of mast portions from the detachable rod member.

The present invention also provides a method of treating a mammalian myocardium having progressive dilation, e.g., of a left ventricle thereof. Preferably, the method includes surgically introducing a catheter device into a mammalian pericardium which can be done through a sub-xyphoid or optical entry point; introducing and positioning plural support members into the pericardial space with the catheter device; positioning an inflatable member between adjacent support members, e.g., by pulling a line through a pulley or spindle portion disposed in the support member or by pushing the inflatable member between adjacent support members using a rod member or tube; and introducing a fluid into the inflatable member to apply pressure to the myocardium. A fluid can also be inserted into the pericardial space to distend adjacent tissues and thereby aid in the extension of the support members into the pericardium.

Optionally, the method further comprises detaching the inflatable members and the support members from the delivery rod or tube member and/or adjusting fluid pressure in the inflatable member. The procedure can be performed under fluoroscopic and/or echo-cardiographics guidance. Hemodynamic monitoring can be used to confirm location and operation of the device.

A further embodiment of the invention employs an implant that can be inserted from an insertion device using rods that are directed into position by the user in a single stage insertion process. The inflatable member is inserted through a distal opening of the insertion device from a folded delivery configuration to an unfolded or deployed configuration. The inflatable member has a plurality of inflatable sections each having a fluid port that can be connected directly to one or more reservoirs or to a single reservoir with a switching manifold.

The implantable system can include a pump and control system that is programmable for each patient and can include sensors for feedback control or pacing leads or conductive elements to control pacing of the heart. This control system can be incorporated into an implant housing that is sized to fit in the abdominal cavity.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 10 shows a series of sectional views of embodiments of a pericardial reinforcement device in the deployed and inflated configuration depicting optional inner wall profiles of the device. FIG. 10A shows a device that has uniform contact and uniform pressure (arrows) over the left ventricle. FIG. 10B shows a device that concentrates increased inward pressure (arrow) against a portion of the left ventricle (LV). FIG. 10C is a schematic representation of the device shown in FIG. 10A. FIG. 10D is a schematic representation of the device shown in FIG. 10B. FIG. 10E is a schematic representation of a device having a ribbed inner wall. FIG. 10F is a schematic representation of a device having a ribbed inner wall and a collar at the top end for retention. FIG. 10G depicts schematically a device having a separately inflatable outer chamber.

FIG. 11 shows a series of sectional views representing an embodiment of a single-stage non-invasive deployment process of a pericardial reinforcement device using a catheter-based approach. FIG. 11A depicts a catheter pre-loaded with an inflatable sail attached to support elements. FIG. 11B shows a cross-section through the loaded catheter of FIG. 11A. FIG. 11C shows the catheter system with a pericardial reinforcement device partially deployed around the apex of the heart.

FIG. 12 shows a series of sectional views representing an embodiment of a two-stage non-invasive deployment process of a pericardial reinforcement device using a catheter-based approach. FIG. 12E shows the catheter system with partially deployed support elements. FIG. 12F shows the catheter system with the support elements fully extended from the catheter and in position around the heart. FIG. 12G shows the system with partially deployed sail being positioned along the pre-positioned support elements by pushing on the rod elements using the uppermost portion of the catheter. FIG. 12H shows the system with sail fully extended along the support elements.

FIG. 15 schematically illustrates the use of lines or rod elements to deploy the inflatable sails of a pericardial reinforcement device. FIG. 15D shows how the positioning line and support element are removed from the installed pericardial reinforcement device. FIG. 15E shows the support element fully removed and the sail ready for inflation. An alternative embodiment is shown in FIG. 15F, in which the support element has been pre-positioned around the heart, and a rod element is inserted into the guide tube. In FIG. 15G, the rod element of FIG. 15F is pushed to extend the sail out of the catheter and along the support element into position around the heart. In this embodiment, the guide tube encloses the support element as the device is moved into position. FIG. 15H shows the pericardial reinforcement device in deployed position. In FIG. 15I, the support element and rod element have been retracted from the guide tube. In FIG. 15J the support element and rod element have been fully removed and the pericardial reinforcement device is in fully deployed and ready for inflation.

FIG. 17 presents a series of schematic illustrations of an embodiment of a process of deployment of a pericardial reinforcement device.

FIG. 19A shows a cross-section of a deployed and inflated pericardial reinforcement device surrounding the heart. This embodiment has a single inflatable chamber. FIG. 19B shows an embodiment of a pericardial reinforcement device that exerts increased pressure at a selected location on the left ventricular wall (arrow). This embodiment has a single inflatable chamber, but exerts differential inward pressure based on its geometry. FIG. 19C shows an embodiment of a pericardial reinforcement device having four inflatable chambers, each fitted with a separate fill line for differential application of inwardly directed pressure. Use of greater fill pressure in the chamber adjacent to the left ventricle is used to apply selectively greater pressure to that area.

DETAILED DESCRIPTION OF THE INVENTION

The present invention describes devices, systems, and methods for minimally-invasively delivering a pericardial reinforcing device into the pericardial space about a mammalian myocardium, i.e., heart, and, more particularly, to devices, systems, and methods for minimally-invasively delivering an inflatable, pericardial "sail" into the pericardial space; wrapping the "sail" around some portion of the myocardium; and inflating the "sail" to apply a confining pressure to the myocardium.

Figure 2:
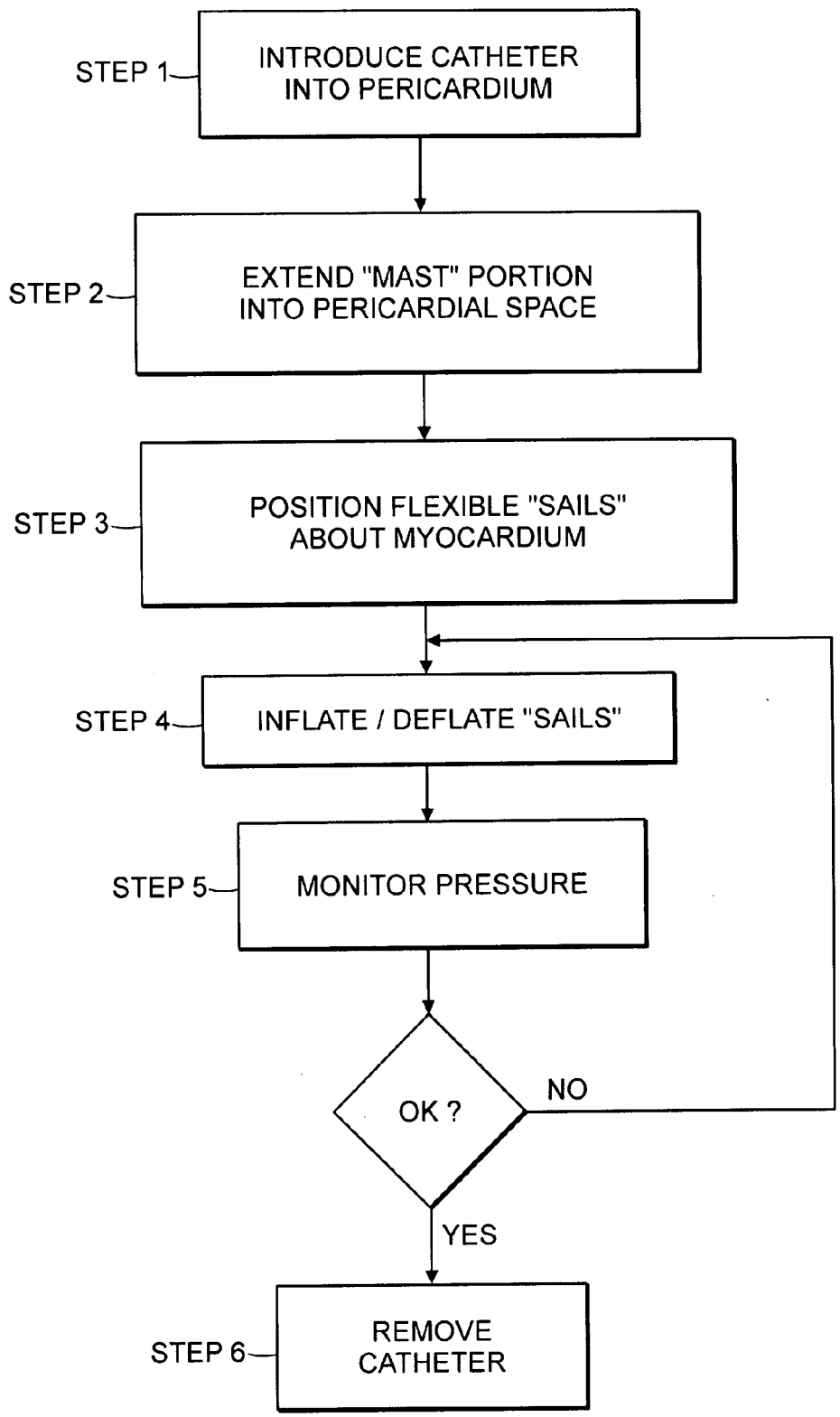
FIG. 2 provides a flow chart of a method for providing minimally-invasive pericardial confinement according to the present invention.

For convenience, the devices and systems of the present invention will be described in the context of their use in the medical process shown in FIG. 2. FIG. 2 provides a flow chart of a method for minimally-invasively delivering an inflatable, pericardial "sail" into the pericardial space; for wrapping the "sail" around some portion of the myocardium; and for inflating the "sail" to apply a confining pressure to the myocardium. Those skilled in the art will be familiar with standard or routine medical procedures for use in conjunction with the present invention.

Figure 1:
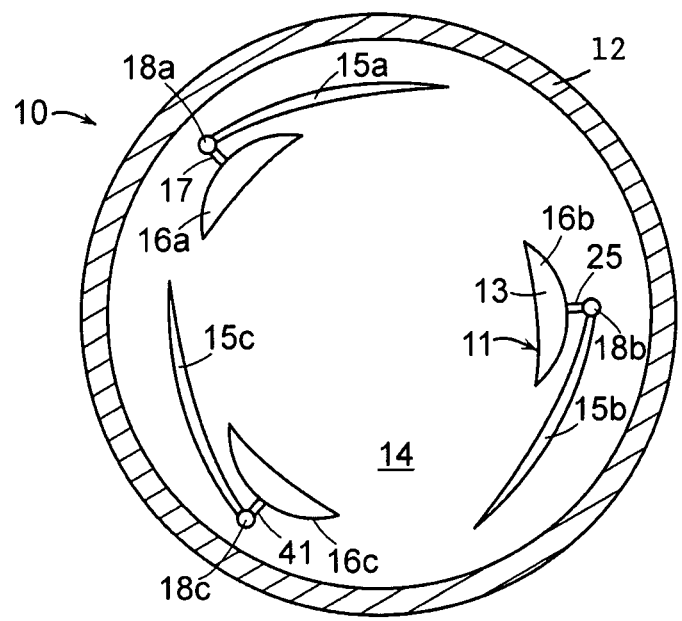
FIG. 1 provides a diagram of a system and device for providing minimally-invasive pericardial confinement according to the present invention.

Referring to FIGS. 1 and 2, in a first step, a catheter 10 is introduced into the pericardial space, or pericardium, about the myocardium (STEP 1). The pericardium can be entered using a sub-xyphoid approach or, alternatively, an apical approach. The introduction procedure can be performed using fluoroscopic and/or echocardiographic guidance to position the distal end, i.e., the internal end, of the catheter 10 at a desired location within the pericardium. Confirmation of the location of the distal end of the catheter 10 within the pericardium can be performed hemodynamically.

The catheter 10 includes a proximal end, which remains external of the mammalian subject or patient during the procedure, and an internal, distal end. The catheter 10 is tubular in shape and includes an outer portion 12 and an inner portion, or lumen 14. The outer portion 12 can be made of a flexible but axially stiff, plastic material, such as those materials typically used for manufacturing catheters for cardiac catheterization.

Structured and arranged inside or within the lumen 14 of the catheter 10 are a plurality of extendable support elements 16a, 16b, and 16c, or "masts". The masts are substantially low profile and can include an outer portion 11 and an inner portion, or inner passage 13. The masts can also be made of a flexible but axially stiff, plastic material. The ends of the masts or outer surface 11, which may contact the epicardial surface, are soft to prevent damaging or scarring the same. Preferably, there are at least three masts 16a, 16b, and 16c inside the catheter 10.

Structured and arranged inside or within the inner passage 13 of each mast 16a, 16b, and 16c is a positionable and detachable rod element about which is configured, e.g., fixedly attached, an inflatable member 15a, 15b, and 15c, or "sail". Rod elements 18a, 18b, and 18c can also be made of a flexible, plastic material. The sails can be made from soft, flexible materials, such as are used for pulmonary artery balloons or silicone breast implants.

Figure 3:
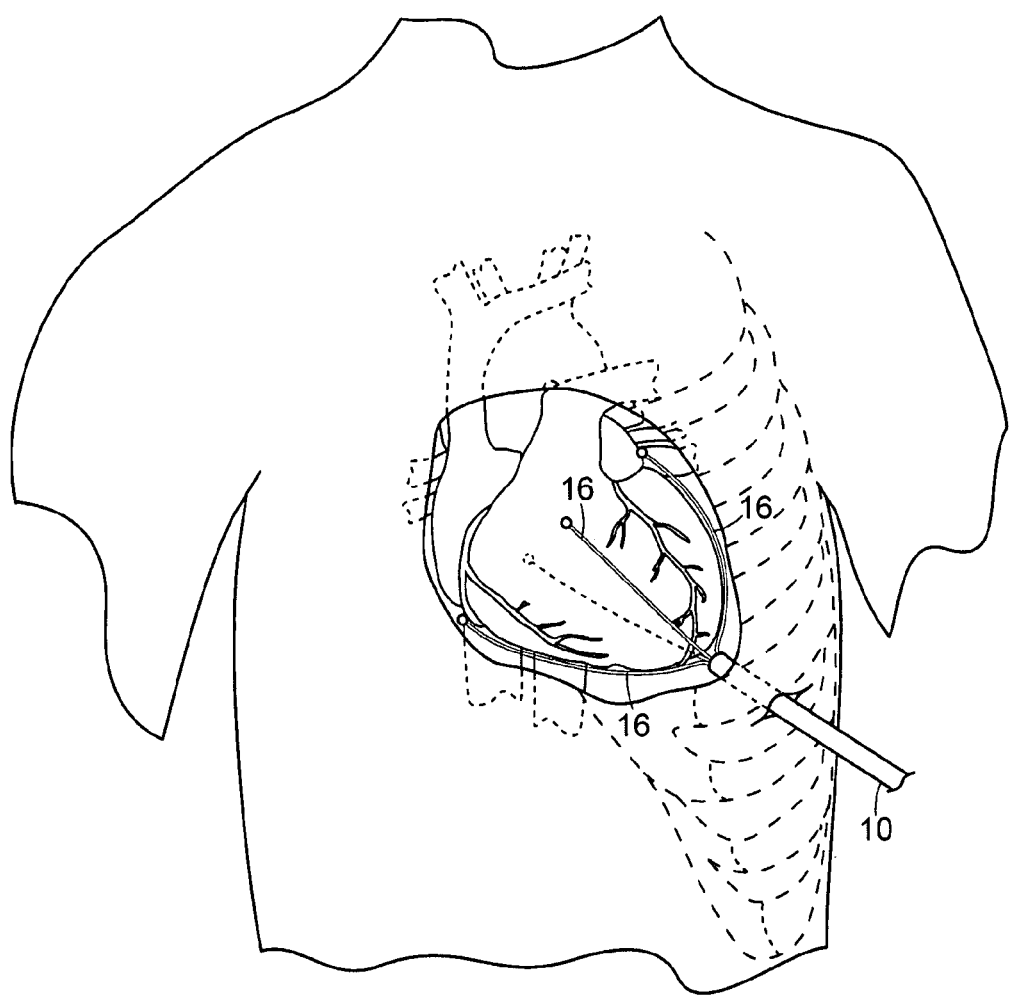
FIG. 3 shows illustratively the step of extending the "masts" in accordance with the present invention.

Referring to FIG. 3, after the catheter 10 is introduced and positioned within the pericardium (STEP 1), the masts can be extended from the distal end of the catheter 10 into the pericardial space (STEP 2). Each mast is separately movable, so that the masts can be positioned where desired. To facilitate extension of the masts 16a, 16b, and 16c in the pericardium (STEP 2), the outer surface of the outer portion 11 of the masts can be pre-lubricated and/or small amounts of fluid can be introduced into the pericardium through open space in the lumen 14 and/or through a fluid conduit 19 provided in the lumen 14 for that purpose.

Figure 4:
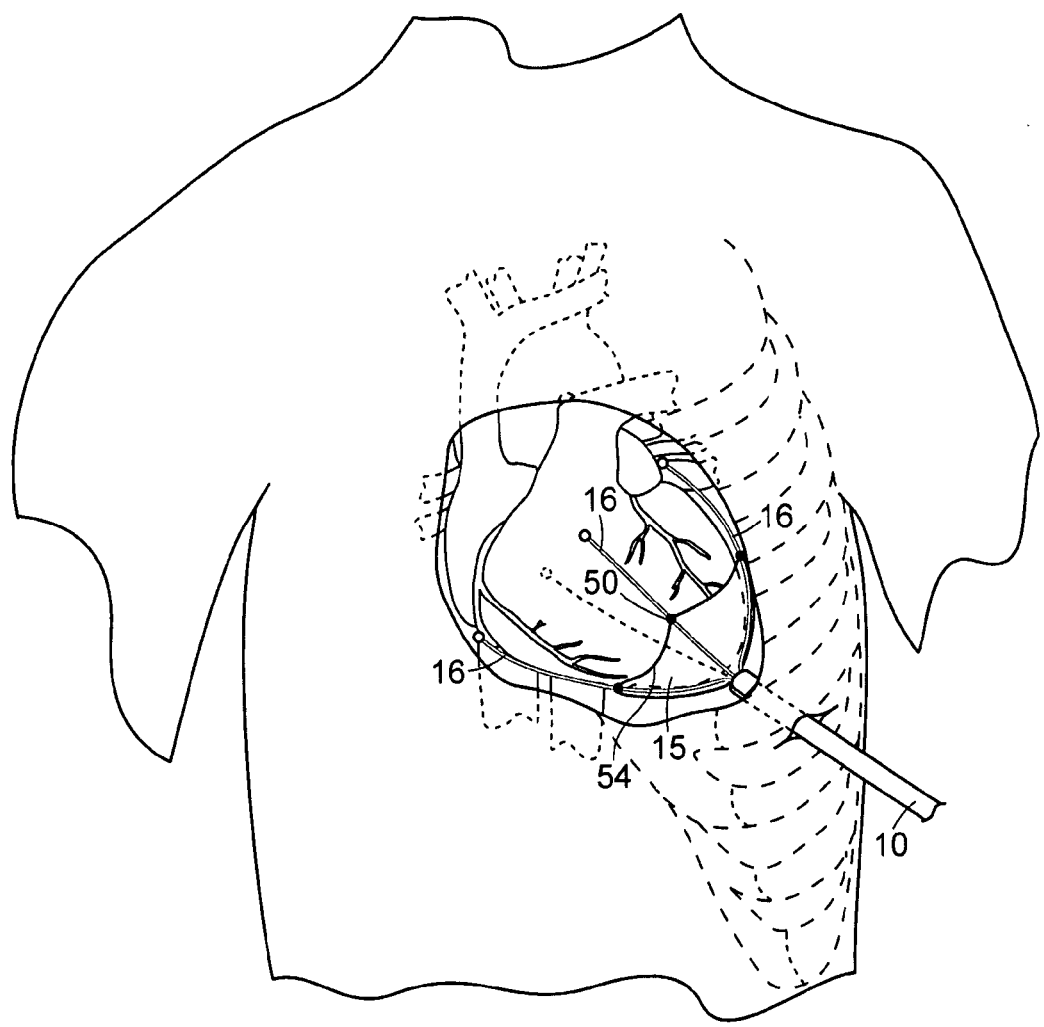
FIG. 4 shows illustratively the step of "hoisting the sails" in accordance with the present invention.

Referring to FIG. 4, after the masts are extended and positioned about the myocardium (STEP 2), the sails 15a, 15b, 15c are "unfurled" and moved from a first position stored within the catheter to a deployed position on the epicardium (STEP 3). In one aspect of the invention, rod elements 18a, 18b, and 18c are used to position the sails. More specifically, a coupler such as a rail portion 17 can be structured and arranged on the peripheral surface 21 of the outer portion 11 of member 16a. Rod element 18a can be structured and arranged to include a groove 23 that is operationally associated with and linearly translatable along the rail portion 17 of member 16a. Alternatively, a groove 22 can be structured and arranged within the inner peripheral surface 21 of the outer portion 11 of member 16b. Rod element 18b can be structured and arranged to include a rail portion or guide 25 that is operationally associated with and linearly translatable in the groove 22 of member 16b. In yet another alternative, the rod member 18c is free to move relative to member 16c or can have coupler 41.

Once the masts have been positioned about the myocardium (STEP 2) properly and where desired, the rod elements are forcibly advanced along the rail portion 17, in the groove 22, pulling the sail as the rod element advances (STEP 3).

Figure 5:
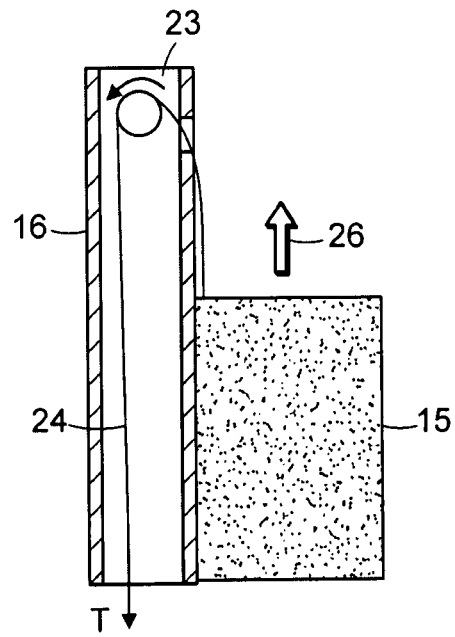
FIG. 5 shows illustratively an alternative for "hoisting the sails" using an internal pulley and pulling mechanism in accordance with the present invention.

Referring to FIG. 5, in another aspect of the invention, instead of using rod elements 18a, 18b, and 18c to position the sails on the epicardium (STEP 3), the sails can be "hoisted" using a small pulley device 23, or spindle, that can be structured and arranged at or near the distal end of the mast. More specifically, a pulling mechanism 24, e.g., wire, string, thread, filament, and the like, can be releasably attached to the sail. The free-running end of the pulling mechanism 24 can be routed about the pulley device 23 and, then, out the proximal end of the catheter 10. Applying a pulling or tugging force T to the free-running end of the pulling mechanism 24 causes the sail to be raised, or "hoisted", up the mast. The pulley device 23 can be structured and arranged so that the sails can be hoisted from outside the masts or, alternatively, can be hoisted from within the inner passage 13 of the masts.

Figure 6:
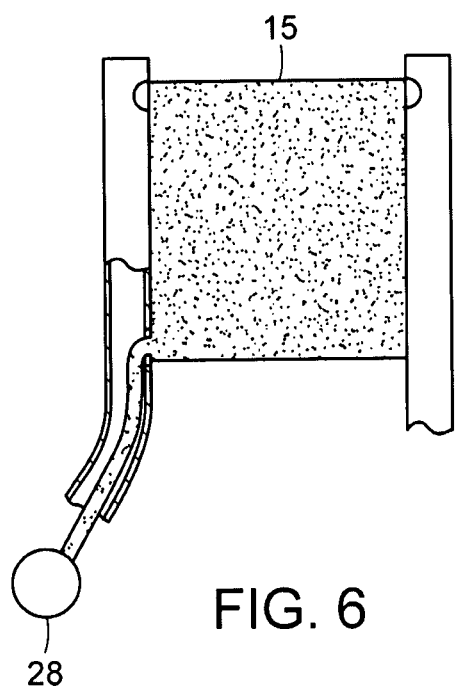
FIG. 6 shows illustratively a pressure measuring device for monitoring, measuring, and adjusting the pressure level in the sails in accordance with the present invention.
Figure 7:
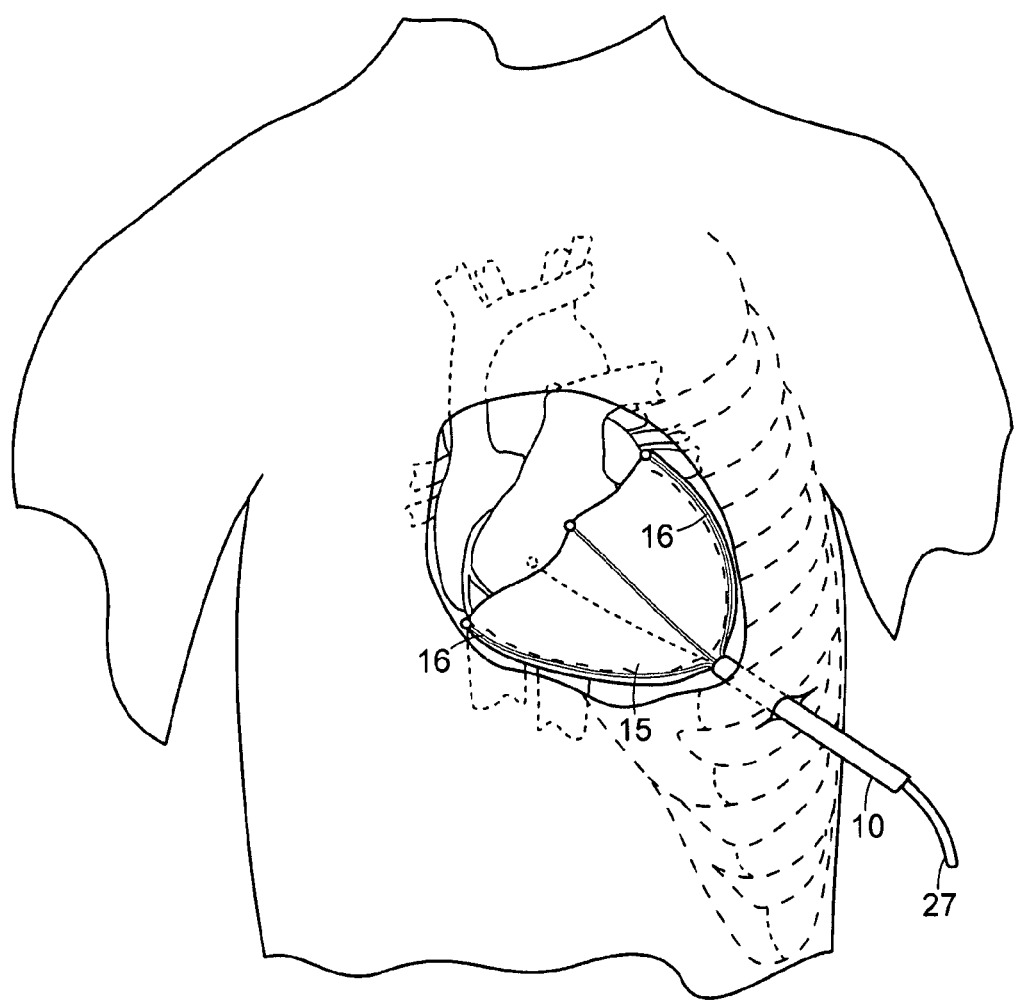
FIG. 7 shows illustratively the step of inflating or deflating the sails in accordance with the present invention.

Referring to FIGS. 6 and 7, once the sails have been positioned about the myocardium (STEP 3), fluid, e.g., compressed air, gas, liquids, and the like, can be introduced into the inflatable sails, e.g., via a filling tube 27, to provide a desired confining pressure (STEP 4), e.g., to the left ventricle. Preferably, a device for measuring the fluid pressure 28 in the sails, e.g., a pressure gauge, pressure meter, pulmonary artery catheter, and the like, is in operational association with the filling tube 27, to measure and to monitor the pressure exerted on the myocardium (STEP 5). Accordingly, when the pressure inside the sails is too high or not high enough, the sails can be deflated or inflated, respectively, to achieve a desired confining pressure.

In yet another aspect of the present invention, each inflatable member 15a, 15b, and 15c disposed between adjacent support elements 16a, 16b, and 16c, respectively, is separately inflated and controllable. Consequently, the confining pressures on different portions of the myocardium that are covered by different portions of the sail, can be varied as necessary or desired. Accordingly, when there are three inflatable members 15a, 15b and 15c, the filling tube 27 can include three separate fluid conduits, each in operational association with a discrete inflatable member 15a, 15b or 15c and each being monitored a dedicated pressure gauge 28 (STEP 5).

Once the pressure in the sails is at a desired level (STEP 5), the catheter 10, detachable rods, and any other portions of the system that will not remain internalized in the mammalian subject can be removed (STEP 6), leaving the masts and inflated sails in place. The catheter 10 and rod members 18a, 18b, and 18c are structured and arranged to easily detach from the masts and sails and the catheter to be easily removed from the incision.

Figure 8:
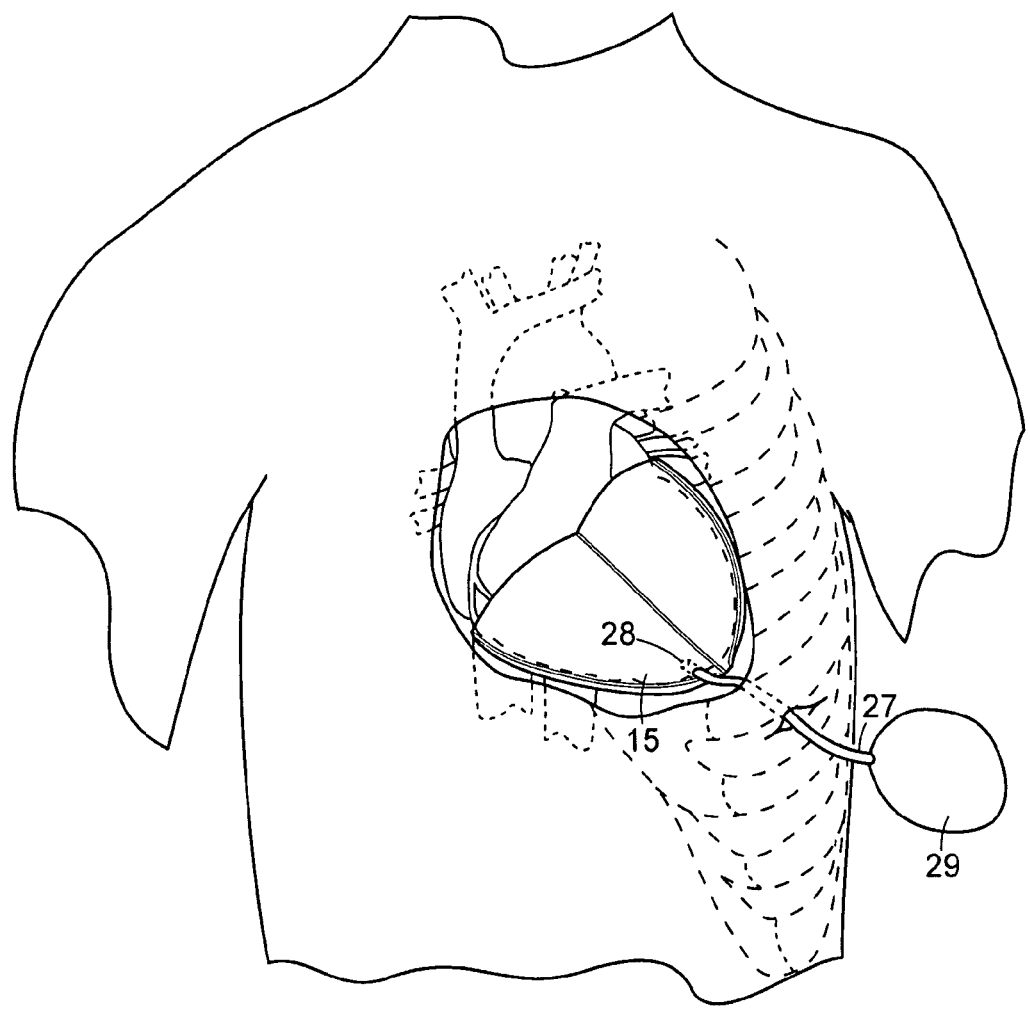
FIG. 8 shows illustratively the step of removing the catheter and masts and attaching a pouch to the filling tube for further pressure monitoring in accordance with the present invention.

In still another aspect of the invention, the filling tube 27 remains internalized, to provide means for monitoring, measuring, and adjusting the fluid pressure in the sails for as long as necessary. Referring to FIG. 8, the filling tube 27 is in operational association with an infusion port 28 that is external to the mammalian subject. A pouch 29 that contains the external portion of the filling tube 27 and the infusion port 28 can be attached to the filling tube 27 at or near the xyphoid or apical point of entry.

Figure 9:
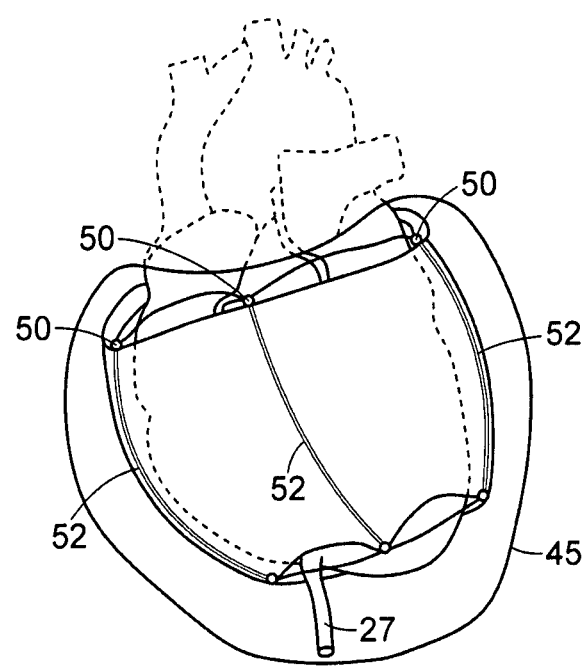
FIG. 9 shows an embodiment of a pericardial reinforcement device in the deployed, inflated configuration within the pericardium and surrounding the ventricles of the heart.

FIG. 9 shows a fully installed pericardial reinforcement device fitted around the ventricles of the heart and positioned within the pericardium 45. The device is positioned with the continuous distal edge 54 of the inflated member approximately aligned at the A-V junction, or near the top of the ventricles. Distal edge 54 optionally can be reinforced with a stiffening structure such as a wire or band of metal, plastic, or fabric. Distal edge 54 also can take the form of a seam or weld joint in the sail materials, e.g., where the materials are glued or sewn together. In this embodiment, guide tubes 52 are present on the exterior surface of the sails. In the embodiment shown, an attachment site 50 is present near the top end of each guide tube. The guide tubes 52 were used to align the inflatable member with support elements, rod elements, or lines during deployment of the device. The support elements, rod elements, or lines can be attached to the inflatable member at attachment sites 50. Typically, one support element, rod element, or line is reversibly attached at each attachment site. After the desired final placement of the device is achieved, then the support elements, rod elements, or lines are detached from the attachment sites and retracted back into the catheter, either before, during, or after inflation of the inflatable members. Depending on the chosen deployment method, either support elements, rod elements, lines, or combinations of these may be used to position the pericardial reinforcement device, although generally only one type of structure will be attached at the attachment sites (e.g., support elements and rod elements are used together for deployment, but only the rod elements are attached to the attachment sites).

Referring to FIG. 10, a variety of textures or structural profiles can be used on the inner surface of the inflatable members that are in contact with the heart. The device shown in FIG. 10A, and depicted schematically in FIG. 10C, has a smooth texture, which provides evenly distributed force where the inflated device contacts the heart. Alternatively, a greater inwardly directed constraining force can be focused over a chosen area, such as all or a portion of the left ventricle, by the use of a pressure point or area 58 as shown in FIG. 10B and depicted schematically in FIG. 10D. Pressure point or area 58 is a protrusion of the inner wall of the inflatable member which results from the geometry of the inner wall material. When inflated, such a pressure point results in greater pressure at its point of contact with the heart than the pressure produced by the surrounding portion of the inflatable member that lacks such a protrusion. The size and shape of one or more pressure points 58 can be chosen as desired to achieve the desired shape and intensity of the zone of applied inward pressure. Optionally, the pressure point can be accompanied by, e.g., surrounded by, a corresponding outwardly deflecting profile in the region of the inflatable member surrounding the pressure point, to provide a zone of a selected pressure surrounded by a zone of lower pressure, or zero pressure. One or more such zones of selectively applied pressure can be employed to define one or more selective treatment areas. For example, treatment can be selectively applied to regions of the myocardium damaged by a previous ischemic event or infarction. Alternatively, zones of lower or zero inward pressure can be selectively applied to territories supplied by one or more chosen coronary arteries, such as the left anterior descending artery, or to an aneurism.

FIG. 10E illustrates a ribbed design, which can be used to facilitate retention of the device in the original deployment position. The ribs can be aligned horizontally to prevent downward migration of the device, or the ribs can be aligned vertically to prevent twisting or rotation of the device. A desired combination of horizontal, vertical, and/or diagonal ribs can be used. The ribs can be formed by designing the inner wall of the inflatable member to produce small protrusions when inflated. Alternatively, structures such as wires, bands, seams, rails, hooks, or barbs can be added to the inner surface of the inflatable member which contacts the epicardium, or embedded within the inner wall material, a seam, or a pocket between the inner and outer walls. As shown in FIG. 10F, a collar structure 56 can be formed, e.g., at or near the top of the inflatable member, in order to hold the device in place and to resist downward migration towards the apex of the heart. A collar 56 can be formed from a ring-shaped pressure point that surrounds the heart, e.g., at or near the A-V junction, or near the top of the ventricles. Alternatively, such a collar can be formed from segments, interrupted for example by welds, joints, or seams between inflatable elements of the device. The collar 56 can also be constructed from one or more separately inflatable elements, so that collar pressure can be separately regulated. Collar 56 can also be formed from structural material, such as a wire, band, rail, or seam added to the exterior surface of the inner wall of the device.

The magnitude of inwardly directed pressure in a pericardial reinforcement device can be from about 1 to about 10 mm Hg, or from about 3 to about 8 mm Hg, or from about 1 to about 8 mm Hg. Preferably, the inward pressure is about 3 mm Hg. The magnitude of the inward pressure at a pressure point can exceed the inward pressure of the overall device or of the area surrounding the pressure of the device by about 1, 2, 3, 4, or 5 mm Hg, or more.

A percutaneous access device such as a tubular probe or catheter system for non-invasive deployment of a pericardial reinforcement device according to the invention can be configured in a variety of different ways, e.g., depending on the desired method of deployment. In one embodiment, the device is deployed by using 3 or more rod elements, preferably 4, that are attached directly to one or more inflatable members via attachment sites.

Referring to FIG. 11, one such "single stage" tubular assembly contains a guidewire tube 30 along its central axis. The device is inserted into the pericardial space by inserting the proximal end of previously implanted guidewire 31 into guidewire tube 30 and sliding the tube or catheter along the guidewire, through an intercostal or sub-xyphoid incision, and into the pericardial space below the apex of the heart. FIG. 11A depicts the pre-loaded catheter traveling along guidewire 31. The catheter assembly has a proximal section 90, which can be a plunger, and a distal section 92 that contains the pericardial reinforcement device prepackaged for deployment.

In FIG. 11B, which shows a cross-section of the distal section, four rod elements 18 are evenly spaced around guidewire tube 30, and one or more inflatable members 15 are appropriately folded and distributed around the support elements. Preferably, each inflatable member 15, or the entire inflatable assembly, is folded into a pleated pattern similar to that of a paper fan, so as to fit the inflatable members into the catheter and promote an orderly and even unfolding upon extension out the distal end of the catheter and beneath the apex of the heart. Other fold patterns also can be used. Preferably, the folds of the inflatable members are radially distributed in a spiral pattern, such as the pinwheel or whirlpool pattern shown in FIG. 11B. This type of pattern promotes compact loading and smooth deployment of the inflatable members.

Each inflatable member has an inner wall, that faces toward the epicardium when deployed, and an outer wall, that faces the pericardium when deployed. Suitable materials for the outer wall of an inflatable member include non-compliant materials such as polyethylene terephthalate (PET). Compliant materials such as a polyamide material (nylon) or polyvinyl chloride (PVC) can be used for either the inner or outer walls of an inflatable member.

The sites of attachment 50 of the rod elements to the inflatable members can be positioned near the distal ends of rod elements 18. The distal ends of rod elements 18 are preferably fitted with ball-shaped, spherical, or ellipsoidal structures to avoid damage to the heart and other tissues during deployment and positioning. Alternatively, the rod element material can be bent back and away from the heart.

Figure 11D:
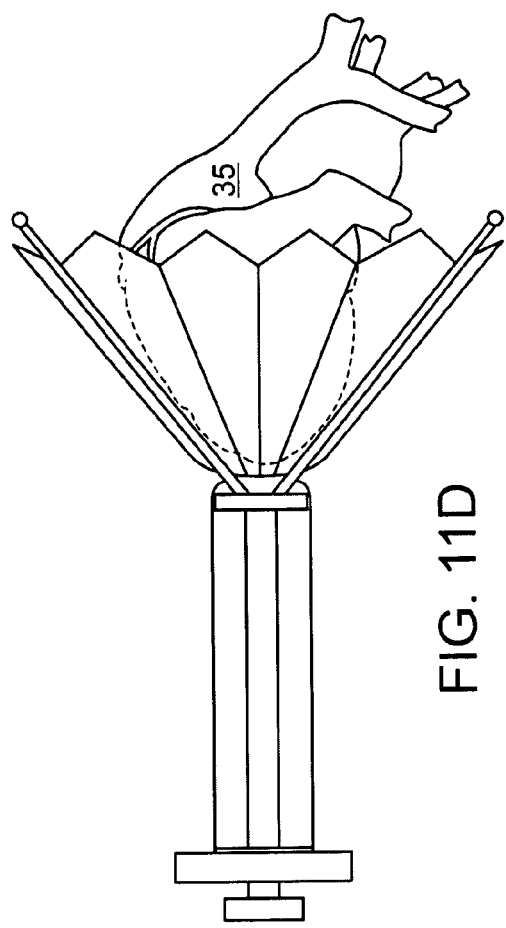
FIG. 11D shows the catheter system with the sail fully extended from the catheter and deployed in position around the heart.

Simultaneous deployment of the rod elements 18 and the inflatable members 15 can be achieved, for example, by the surgeon moving a plunger, a lever, or another structure at the proximal end of the catheter, or attached to a control handle at the distal end of the catheter. In the embodiment depicted in FIG. 11C, pushing on the plunger at the proximal end of the catheter results in the rod elements extending outward from the distal end of the catheter. The rod elements simultaneously push the inflatable members, via the attachment sites, out the distal end of the catheter as well. As the pleated fold of the inflatable members unfolds, it causes the inflatable assembly to open and assume a roughly conical shape which allows it to pass over the apex of the heart. As the plunger is pushed, the rod elements continue to move up and around the heart, and continue to extract and unfurl the inflatable members, which move upwards towards the base of the heart. In FIG. 11D, the rod elements are fully extended, and the inflatable members have been fully extracted from the distal end of the catheter or tube and moved into position around the ventricles of the heart. If necessary, the surgeon can manipulate the catheter at this time in order to position the uninflated inflatable members around the heart. For example the catheter can be moved from side-to-side, slid into the patient, partially withdrawn from the patient, or rotated to achieve the optimum position. Fluoroscopic guidance during the deployment of the device is preferable. To facilitate this, the device optionally can be outfitted with x-ray opaque markings.

Figure 11E:
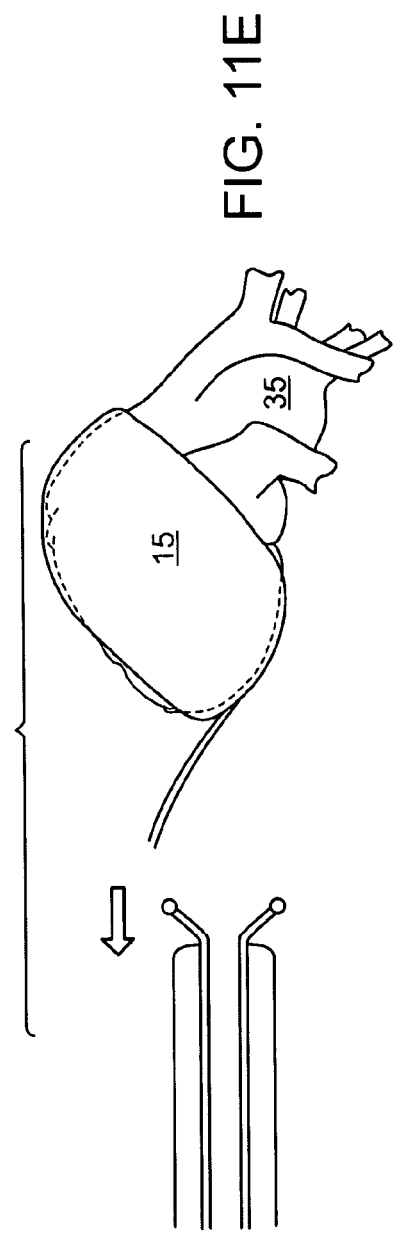
FIG. 11E shows the retraction of the support elements back into the catheter and the fully deployed pericardial reinforcement device, ready for inflation.

After the device is brought into the appropriate position around the heart, the attachment mechanism at the distal end of the rod elements 18, which bind the rod elements to the attachment sites 50 on the inflatable members 15, can be released. For example, a twisting motion of the catheter handle or plunger, or the activation of a button or lever on a catheter control handle can be used to release the rod elements from the attachment sites. Once the rod elements have been uncoupled from the inflatable members, the rod elements are withdrawn into the catheter and the catheter is removed from the subject. The inflatable assembly is then inflated by infusion of fluid to the desired pressure (FIG. 11E).

In another embodiment, the device is deployed using a "two stage" approach. For this approach, a group of 3 or more support elements, preferably 4, are deployed around the heart during the first stage. In this case, the support elements are not attached to the inflatable members. During the second stage, the inflatable members are pushed or raised into position around the heart using the previously placed support elements as guides or tracks, or as a glide surface. In either case, the two-stage approach takes advantage of the support elements to physically uncouple the deployment of the pericardial reinforcement device from the surface of the beating heart during the first phase. Later, once the device is in position, i.e., during the second phase, the device is coupled to the heart by inflation in the absence of the support elements. The two-stage deployment method is shown in FIG. 12.

Figure 12A:
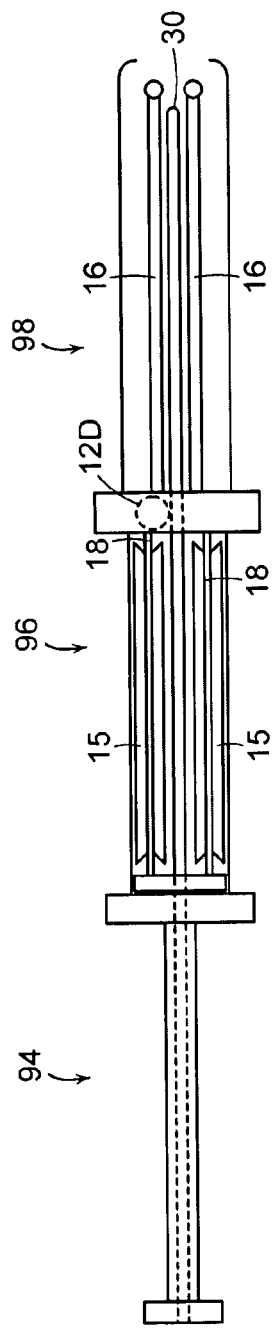
FIG. 12A depicts a catheter pre-loaded with support elements and an inflatable sail attached to rod elements.
Figure 12C:
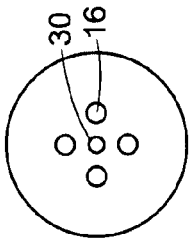
FIG. 12C is a cross-section through the lower portion of the catheter containing the support elements.
Figure 12B:
FIG. 12B is a cross-section through the upper portion of the catheter containing the sails and rod elements.

FIG. 12A shows a pre-loaded catheter assembly for a two-stage deployment of a pericardial reinforcement device according to the invention. Similar to the single-stage catheter assembly, an axial guidewire tube 31 accommodates a guidewire to facilitate the insertion of the catheter into the pericardial space. The two-stage catheter or rigid tubular assembly has a proximal section 94, or plunger, a middle section 96, and a distal section 98. FIG. 12B shows a cross-section of the middle section. In this embodiment, the middle section contains four rod elements 18 disposed around the central guidewire tube 30. Each rod element is reversibly attached to an attachment site on an inflatable member that is packed within the middle section of the catheter. The inflatable members are folded and distributed as described above for the distal portion of the single stage catheter assembly. FIG. 12C shows a cross-section of the distal section of a two-stage catheter assembly. In the embodiment shown, the distal section contains an axial guidewire tube 30, around which are disposed four support elements 16. The support elements 16 are of similar length as the rod elements 18, or slightly shorter than the rod elements in certain embodiments. In some embodiments, the support elements 16 are aligned with, and attached to, the rod elements 18 at the junction between the distal and middle sections of the catheter assembly. In other embodiments, support elements 18 are not coupled to rod elements 18. In such embodiments, the support elements merely form a convenient glide surface or guide, which covers the surface of the heart and against which the device can be deployed.

Figure 12D:
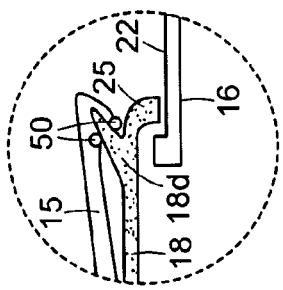
FIG. 12D is a close-up view of one embodiment of the linkage between a rod element of the upper catheter section and a support element of the lower catheter section.

FIG. 12D illustrates the detail of an attachment mechanism that allows the rod elements 18, by means of rail portion 25, to slide up a track or groove 22 in the support elements 16. Rail portion 25 is linearly translatable in groove 22, such that pushing on a plunger attached to rod elements 18 advances the rods 18 toward the distal ends of support elements 16, thereby deploying the attached inflatable members 15. An inflatable member 15 is attached to rod element 18 by, for example, the coupling of an attachment site 50 (a small ring in the embodiment shown) to rod spike 18d. Other arrangements are possible. Advantages of the arrangement depicted in FIG. 12D include: (1) positive displacement of the inflatable members along the support elements by a simple push rod mechanism; (2) distribution of deployment forces according to the distribution of support elements; (3) uncoupling of the deployment of inflatable members from the structural dynamics of the beating heart by the use of previously deployed support elements; (4) automatic uncoupling of rod elements 18 from support elements 16 by pushing the rods off the track at the distal end of the support elements; and (5) automatic uncoupling of rod elements 18 from inflatable members 15 by retracting the rod elements back towards the catheter.

Figure 12I:
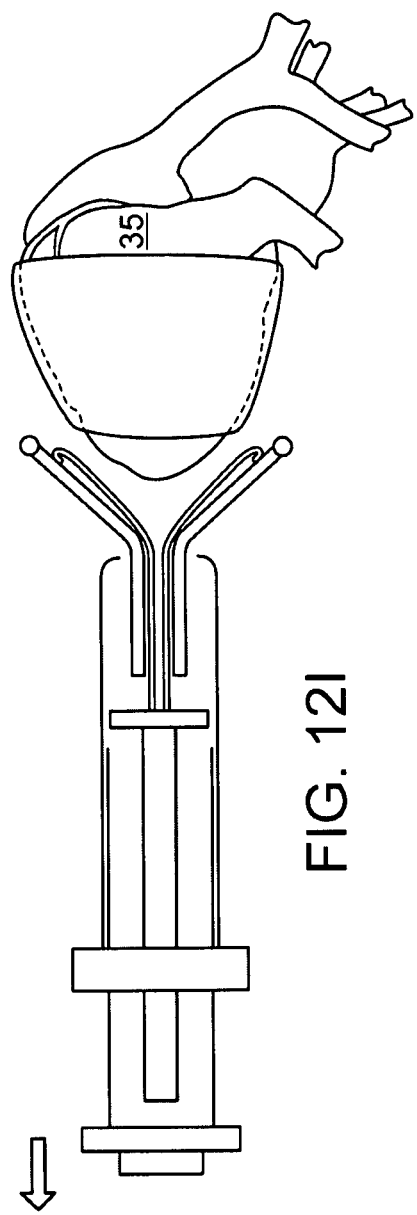
FIG. 12I depicts the catheter system having the reinforcement device in position and inflated and released from the rod elements; the rod elements and support elements have been partially retracted. In an alternative embodiment (not shown), the individual support elements can be extended and retracted separately, e.g., one at a time, to aid in positioning the catheter system for deployment of the sails.

Once the two-stage catheter assembly is in place at the apex of the heart, support elements 16 are extended out from the distal end of the catheter assembly. In the embodiment shown in FIG. 12E, this can be accomplished by sliding the middle section of the catheter assembly into the distal section. After support elements 16 are fully extended and in position around the ventricles (FIG. 12F), the first stage is completed. The second stage is initiated by advancing the rod elements with attached deflated inflatable members 15 (FIG. 12G). As was the case for the single stage approach, the advancement of the rod elements causes the inflatable members to exit the distal end of the catheter and unfold, thereby forming an approximately cone-shaped structure that surrounds the heart (FIG. 12H). The support elements 16 and rod elements 18 are retracted into the catheter by sliding back the middle section, the catheter assembly is removed from the subject, and then the inflatable members are inflated with fluid (FIG. 12I). In other embodiments, the inflation process can be carried out before or during retraction of the rod and support elements.

In a variation of the two-stage process, a set of support elements 16 is advanced into the pericardial space individually rather than as a unit. This can offer flexibility in positioning the support elements around a beating heart. In order to permit this option, an embodiment of the two-stage catheter assembly is used that permits extension of each support element separately. One example of how to accomplish this is by splitting the structure in which the support elements are mounted, and coupling each support element mounting structure separately to a movable portion of the catheter assembly, or to separate controls in a catheter control handle.

Figure 13A:
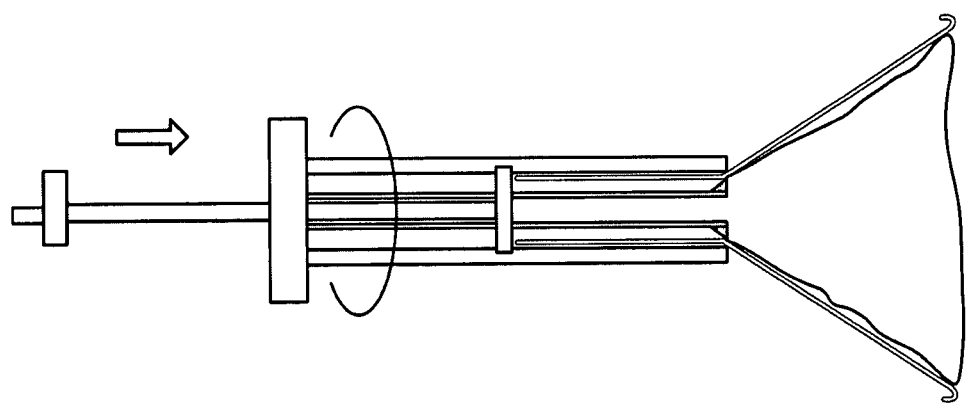
FIG. 13A depicts the use of a splaying mechanism built into the catheter for extending and positioning the support elements around the apex of the heart.
Figure 13B:
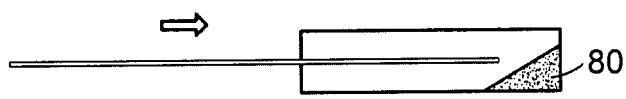
FIGS. 13B and 13C illustrates the use of an angular constriction at the distal end of the catheter to splay the support elements.
Figure 13C:
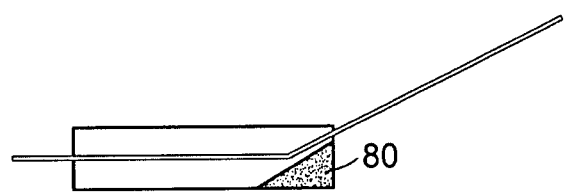

It is instrumental when deploying either support elements or rod elements from a catheter assembly according to the invention to spread or splay the elements so as to accommodate the shape of the heart. One mechanism for splaying such elements is depicted in FIGS. 13A and 13B. By incorporating wedge-shaped forming element 80 at the exit point at the catheter distal end, an appropriate material will be induced to splay when either a rod element or a support element is advanced out of the catheter. Suitable materials include fine metal wires and plastics that can be bent to yield an angular rod-like structure. The support or rod element can be shaped so as to form an angle at the wedge shaped forming element but retain a straight orientation thereafter. One embodiment with this characteristic is a partially rounded flat surface that folds inwardly more easily than it folds outwardly. The edges of the curved cross-sectional profile of the rod or support element can point away from the central axis of the catheter, such that the rod or support element will bend outward at the wedge-shaped forming element, but will resist bending inward, much like the action of a metal tape measure having a similar curved cross-sectional profile. The splay angle of support elements or rod elements as they exit the catheter and approach the heart can be tailored to the size and shape of the recipient heart, or varied as the support elements or rod elements progress upwards along the heart, e.g., to maintain optimum contact. This can be accomplished, e.g., by adjusting the forming wedge at the distal end of the catheter. A control mechanism can be included in the catheter that alters the angle or position of the forming wedge. For example, by tilting the wedge, or by displacing it towards or away from the exiting rod or support elements, the splay angle can be increased or decreased as desired, either before or during deployment. An alternative to splaying the rod or support elements as they exit the catheter is to use pre-formed rod and/or support elements that are compressed into the catheter and assume their pre-formed shape upon exiting from the catheter. Yet another alternative is to use a combination of pre-formed rod and/or support elements whose form is modified upon exit from the catheter using a forming element.

Figure 14A:
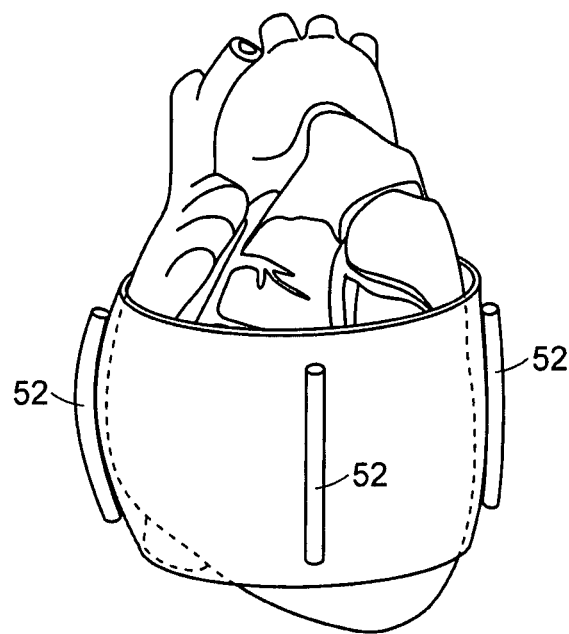
FIG. 14A schematically depicts an embodiment of the pericardial reinforcement device having guide tubes mounted onto the outer wall of the sail to accommodate support elements and/or rod elements.
Figure 14B:
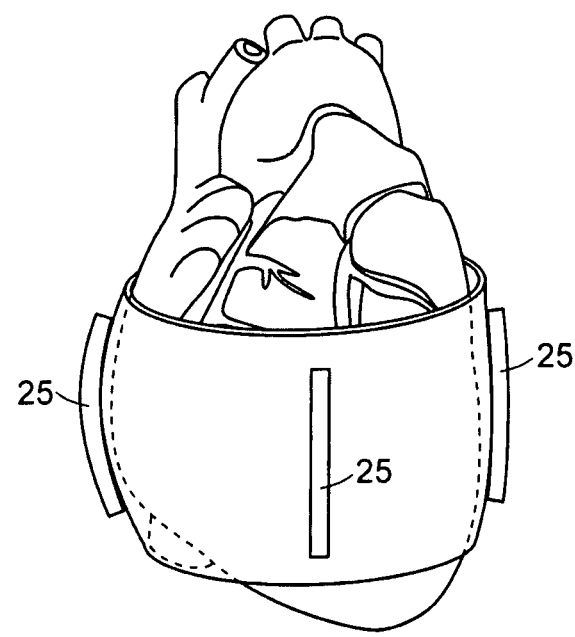
FIG. 14B depicts an embodiment of the device having rails mounted onto the outer wall of the sail to accommodate support elements and/or rod elements.

Either single-stage or two-stage deployment of a pericardial reinforcement device can be assisted by adding certain structures to the outside of the inflatable members, or alternatively having structures run through the inflatable members. Two examples are shown in FIGS. 14A and 14B. The embodiment of FIG. 14A includes guide tubes 52, which can serve to align a rod element 18 (push rod), a line 24 (pull line), or a support element 16 with attachment sites 50 on an inflatable member, and also can maintain an uninflated inflatable member in alignment with a rod element 18, a line 24, or a support element 16, and at some distance from the beating heart, so that the inflatable member does not become entangled or exert too great a drag on the beating heart when being positioned. FIG. 14B shows a rail as an alternative guide structure. Such a rail can couple to a track or groove in a support element 16 or a rod element 18.

Figure 15A:
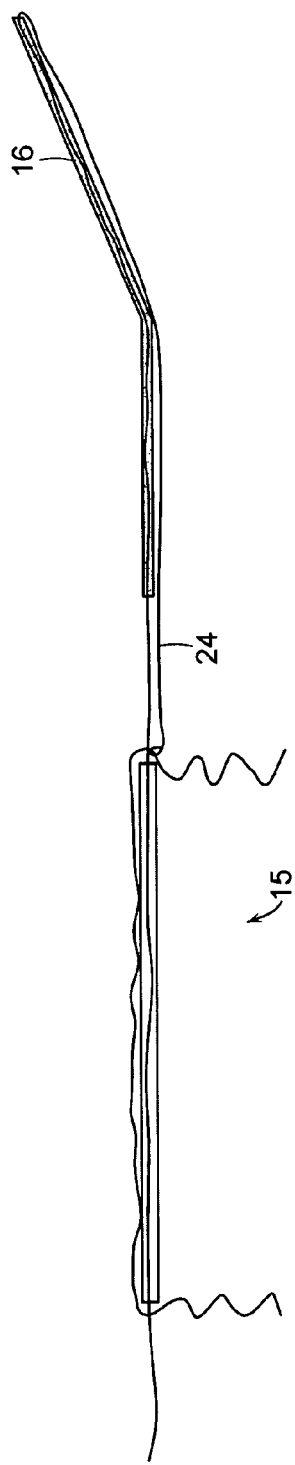
In FIG. 15A, a line bound to an attachment site at the top end of an inflatable sail runs through the lumen of a support element, back down through a guide tube attached to the sail, and continues out through the catheter.
Figure 15B:
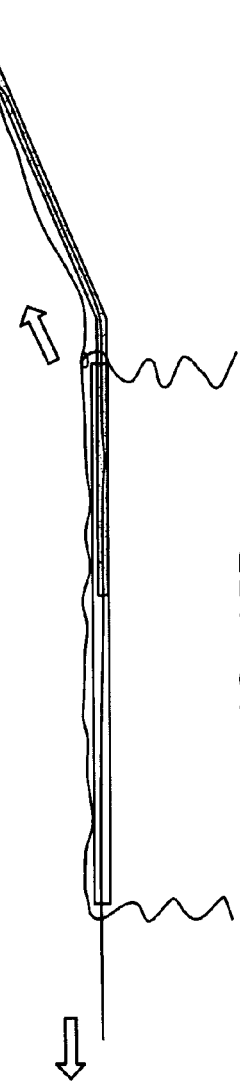
FIG. 15B depicts how the line from FIG. 15A, after exiting the proximal end of the catheter (not shown) can be manipulated by the surgeon to deploy the sail.
Figure 15C:
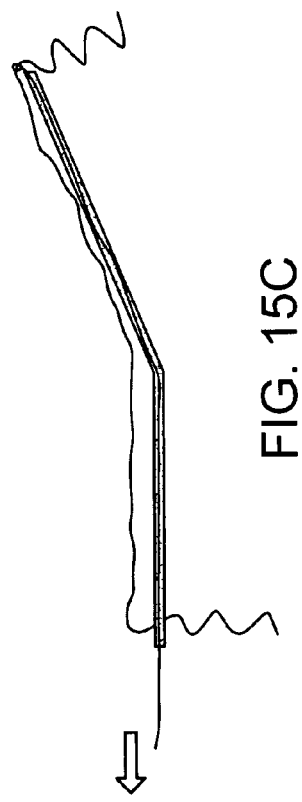
In FIG. 15C, the sail has been raised into position and the positioning line has been detached from the sail.

The use of guide tubes is illustrated in FIG. 15. In FIGS. 15A-15E, guide tubes 52 are used together with pull lines 24 to direct the positioning of inflatable member 15. In this embodiment, support element 16 is hollow, permitting line 24 to be routed through support element 16, around a pulley 23 or spindle at the distal end of support element 16, and back down through guide tube 52 and out the proximal end of the catheter (FIG. 15A). When line 24 is pulled through or out of the catheter in a proximal direction, inflatable member 15 is hoisted over support element 16 (FIG. 15B) and out to its distal end (FIG. 15C). Support element 16 is then withdrawn from the guide tube (FIG. 15D), leaving inflatable member 15, with attached guide tube 52, in position around the heart (FIG. 15E).

FIGS. 15F through 15J illustrate an embodiment employing rod elements instead of lines. Rod element 18 is initially positioned within sail-mounted guide tube 52 (FIG. 15F). The guide tube is then slid over support element 16, which was previously positioned around the heart (FIG. 15G), until inflatable member 15 is fully inserted to the distal end of support element 16 (FIG. 15H). Rod element 18 and support element 16 are then withdrawn, together (FIG. 15I), leaving inflatable member in position around the heart, ready for inflation (FIG. 15J).

Figure 16B:
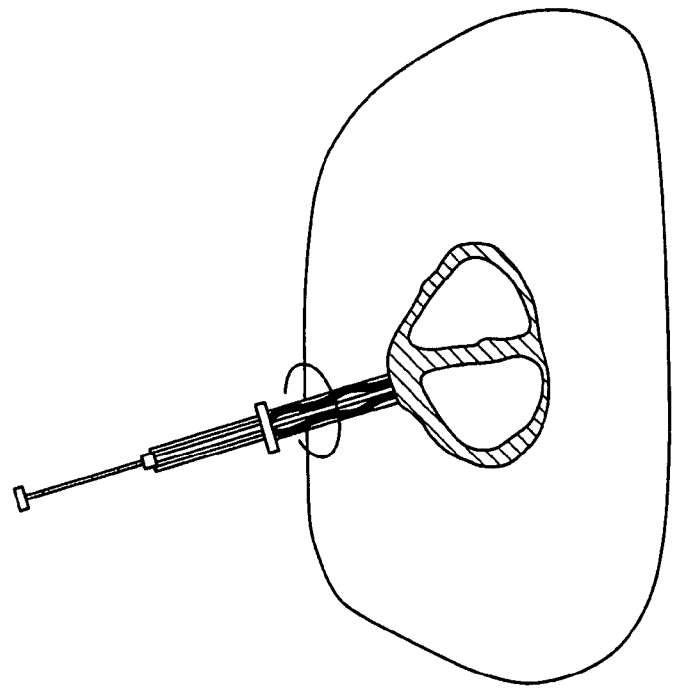
FIG. 16B shows a cross-sectional view of the approach in FIG. 16A.
Figure 16A:
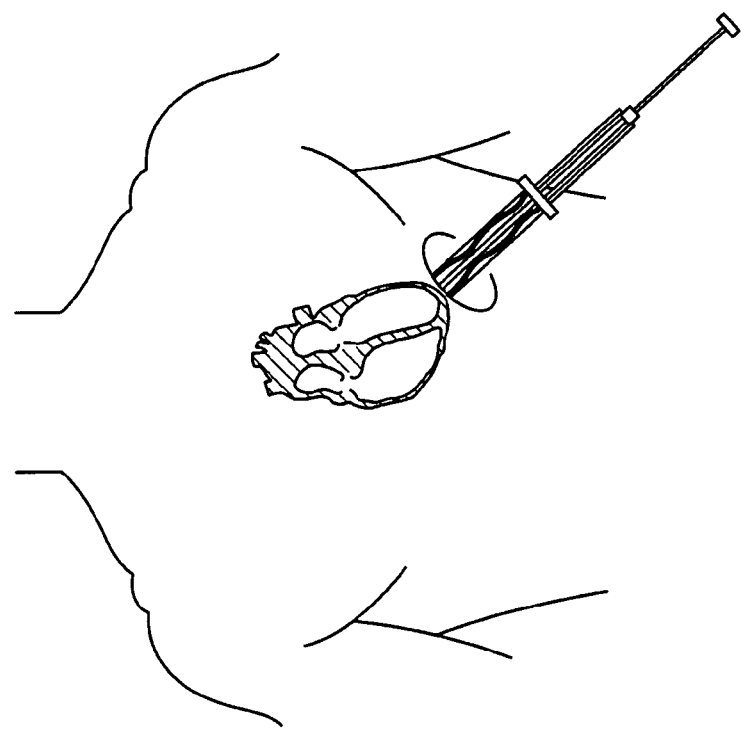
FIG. 16A is an external view of an intercostal approach to access the pericardial space using a catheter device of the invention.

FIG. 16 displays a two-stage catheter embodiment in position at the apex of the heart, prior to extension of the support elements. FIG. 16A shows a front view, using a left intercostal approach, and FIG. 16B shows a cross-sectional view.

FIG. 17 provides an overview of deployment of a pericardial reinforcement device using a two-stage catheter assembly. Percutaneous access of the pericardial space can be performed either via a subxyphoid approach or in the apical position (4th intercostal mid clavicular space) at 45 degrees to the patient (see Laham et al., Clin Cardiol (1999) 22:I6-9; Laham et al., Catheter Cardiovasc Interv (1999) 47:109-111; and Laham et al., Catheter Cardiovasc Interv (2003) 58:375-381, each of which is incorporated herein by reference). This can be accomplished, for example using a Tuohy 17 epidural needle with continuous contrast and saline injection. The needle is attached to a pressure manifold and a 10 cc syringe via a three-way stopcock. In addition, the needle is attached to an EKG monitoring lead. The needle is advanced slowly with diluted contrast instillation. Once intrapericardial location is confirmed, a wire is advanced over which a 10 French sheath is introduced into the pericardial space (FIG. 17B). Following the use of a dilator to enlarge the passageway, the catheter assembly is inserted into position (FIG. 17C) with its distal end below the apex of the heart.

Alternatively, a 5 cm incision can be made in the fourth intercostal space (left thoracotomy) and the procedure as well as the device placement can be performed under thoracoscopic direct vision. Briefly, the patient is intubated into the right main stem bronchus and the left lung is deflated. 10-mm "camera" thoracoport (U.S. Surgical Corporation, Norwalk, Conn.) is inserted in the 4th intercostal space midaxillary line. A 30-degree thoracoscope (Stryker Corporation, Stryker Endoscopy, San Jose, Calif.) is introduced through this port into the chest. Under direct visualization, a 5-mm port is inserted in the eighth intercostal space anterior axillary line. After placing the port, the trochar is removed to allow the introduction of both endoscopic shears and grasper. A pericardial window is made in a longitudinal fashion, exposing a large section of left ventricular myocardium. A port for device insertion is placed directly superior to the apex of the heart, lateral to the sternum and left internal mammary artery. See Thompson et al. (2004) Ann Thorac Surg 78: 303-7.

Figure 17A:
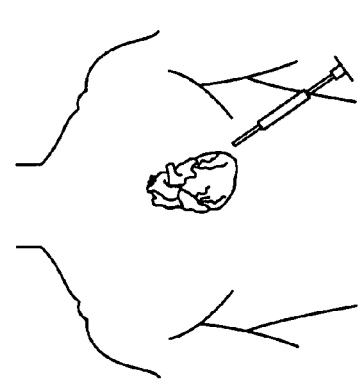
FIG. 17A shows the placement of a blunt-tip needle into the pericardial space at the apex of the heart.
Figure 17B:
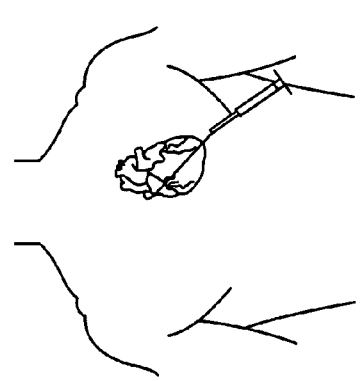
In FIG. 17B, the needle has been exchanged for a catheter, and a guidewire is advanced into the pericardial space.
Figure 17C:
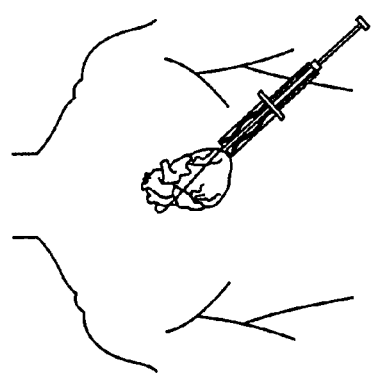
In FIG. 17C, a catheter device containing a pericardial reinforcement device is inserted along the guidewire.
Figure 17D:
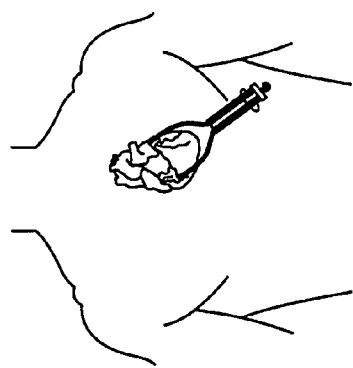
FIG. 17D shows the support elements extended from the catheter and positioned around the heart.
Figure 17E:
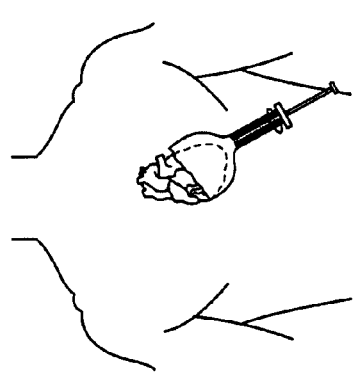
In FIG. 17E, the pericardial reinforcement device is deployed in position around the heart.
Figure 17F:
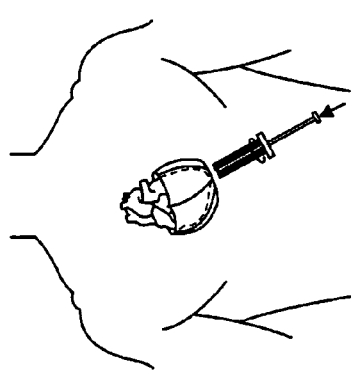
FIG. 17F shows the introduction of fluid into the sails of the pericardial reinforcement device.
Figure 17G:
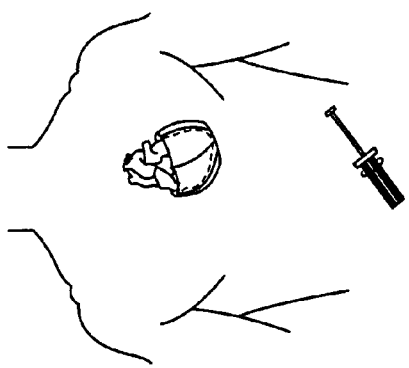
FIG. 17G depicts the fully inflated and deployed pericardial reinforcement device and the withdrawn catheter device.

After the catheter is in place near the heart, the support elements are extended (FIG. 17D), and then the inflatable members are extended along the support elements into position around the ventricles of the heart (FIG. 17E). Fluid is introduced into the inflatable members (FIG. 17F), and the pressure adjusted to apply the desired operating inward pressure. FIG. 17F illustrates an embodiment in which a fluid line runs through the catheter lumen and is attached to one or more fill lines on the inflatable members. After the device is finally installed and adjusted, the catheter is removed and the incision is closed (FIG. 17G).

Figure 18B:
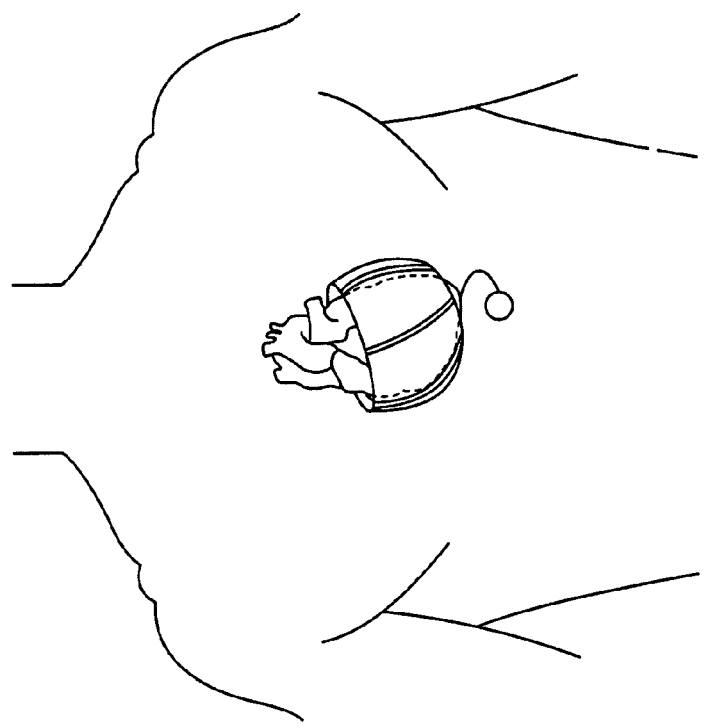
FIG. 18B shows an embodiment of a pericardial reinforcement device with a fill tube attached to an infusion port implanted in the chest.
Figure 18A:
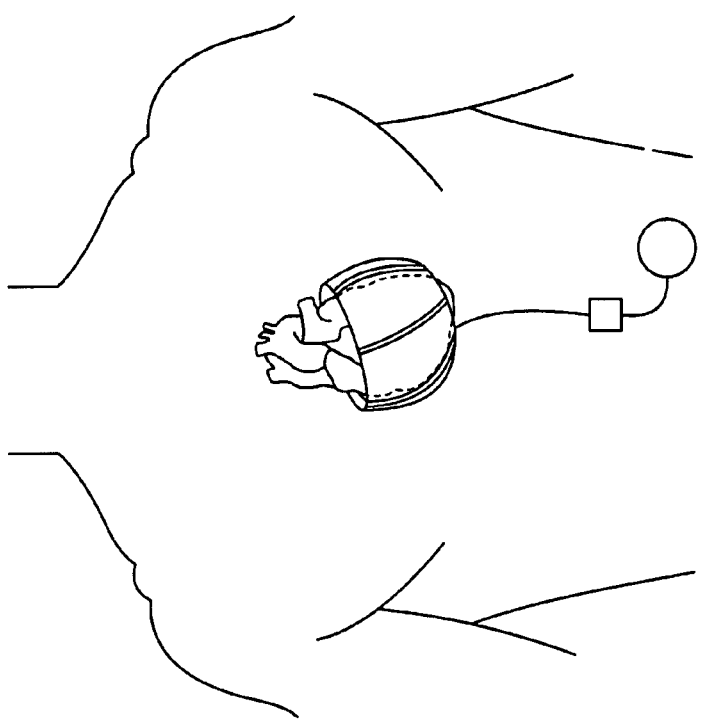
FIG. 18A shows an embodiment of a deployed pericardial reinforcement device having a fill tube attached to a fluid reservoir through a control unit containing a pump. The control unit and reservoir are implanted in the abdomen.

Adjustments to the confining pressure provided by the pericardial reinforcement device can be made following surgical implantation of the device. FIG. 18 demonstrates two embodiments of the device that include structures for adjusting the pressure by adding or removing fluid from one or more inflatable chambers. In FIG. 18A, the fill line from the inflatable member or members is connected to pump 62 which in turn is connected by tubing to fluid reservoir 29. The pump and fluid reservoir can be implanted within the abdomen and connected via a subcutaneous line to the pericardial reinforcement device in the chest. A simpler version is shown in FIG. 18B, having a subcutaneous infusion port connected to the fill line. Fluid can be withdrawn or added through the infusion port using a needle to lower or raise the confining pressure, respectively.

The force exerted on the heart by the device and vice versa can be obtained from a plot of ventricular wall force vs. displacement (stress-strain curve), the slope of which is a function of the properties of the material that the inflatable members are made of, and the degree of inflation. The stress/strain relationship is represented by $S_r = Pd/2t$ and $S_1 = pd/4t$, where P=left ventricular end diastolic pressure (LVEDP), d=ventricular diameter, t=ventricular wall thickness, $S_r$=hoop or radial stress, and $S_1$=axial or longitudinal stress.

From the above equation, the calculated radial tensile strength (TS) of a balloon can be calculated as follows: TS=pd/2t where p=burst pressure, d=diameter (as made), and t=thickness (as made). The pressure exerted inwardly can be adjusted to the strain and outward deformation of the epicardium. Measurement of the epicardial deformation during the cardiac cycle has been previously described (Arts and Raneman, 1980). At its maximum diameter, the filled ventricle in diastole will exert under 5 pounds of force on the constraining device, which is within the linear portion of the stress-strain curve (see Walsh, R, (2005) Heart Failure Reviews 10:101-7). Displacement will be maximum in diastole and minimum in systole. The transmural pressure exerted by the device would be equal to the difference between LVEDP and the pressure exerted by the device (typically 10 mm Hg=15 mm Hg-5 mm Hg). Thus, in a preferred embodiment, on average the device would exert 5 mm Hg of pressure at end-diastole. This can be adjusted based on LVEDP sensed (e.g. by a pulmonary arterial catheter). In the experiments performed by Ghanta et al. (Circulation 115:1201-10 (2007)), the optimal restraint level was determined to be 3 mm Hg in an ovine heart failure model, which allowed for a reduction in transmural pressure that produced improved cardiac mechanics without reduction in aortic pressure or cardiac output.

FIG. 19 demonstrates three embodiments which differ in the application of pressure to the ventricular wall. In FIG. 19A, a single inflatable member 15 surrounds the heart, with approximately uniform contact and uniform pressure from all sides. In FIG. 19B, elevated inward pressure (arrow) is selectively applied to a portion of the left ventricle (LV) by means of a single inflatable member containing a pressure point, i.e., a point of contact with the ventricular wall surrounded by a region lacking contact. The embodiment shown in FIG. 19C has four separate inflatable members, each of which can be adjusted independently of the others by variable filling to obtain a desired pressure.

The inner wall of an inflatable member is flexible and compliant in order to accommodate the dynamic form of a beating heart, and also to accommodate long term changes in size or shape of the heart, e.g., due to progression of cardiac hypertrophy. The outer wall of an inflatable member can be either flexible or inflexible and compliant or non-compliant. Preferably, the outer wall is flexible and compliant. More preferably, the outer wall is less compliant than the inner wall. Differential compliance or elasticity between the inner and outer walls can be advantageous in allowing the inflated device to absorb shape changes during the cardiac cycle without fully transmitting those changes outwardly to the pericardium. This can improve the stability of device placement over time without offering too much resistance to movement of the heart. Maintaining some compliance in the outer wall further permits the device to expand over time, e.g., by adding fill fluid, in order to respond to disease progression, with less increase in inward pressure than would result from a non-compliant outer wall. In some embodiments, the relative compliance of the outer and inner walls is adjusted to the needs of the individual patient. For example, a patient with early stage hypertrophy might be fitted with a device having a more compliant outer wall to accommodate more long term expansion. Both the absolute and the relative compliance of the outer and inner walls also can be varied over the surface of an inflatable member or an assembly of inflatable members to produce differential effects, e.g., different inward pressures, at different regions of the ventricular myocardium.

One embodiment of a pericardial reinforcement device includes a non-compliant outer layer surrounding the inflatable member or assembly of inflatable members. Such an outer layer can be formed, for example, by adding a separately inflatable outer chamber 70 (FIG. 10G) covering the inflatable inner chamber (inflatable member 15). Once the device is in place around the heart, a polymerizable fluid can be introduced into the outer chamber and allowed to polymerize, forming a non-compliant outer layer. The inner inflatable member or members can be inflated either before, during, or after inflation of the outer chamber.

Two or more inflatable members can be joined to form an inflatable assembly. The arrangement of inflatable members within an assembly can include either vertical or horizontal patterns, or other patterns, of individual inflatable members that are joined side-by-side through non-inflatable joints, seams, or welds. Preferred embodiments use a vertical arrangement of inflatable members, i.e., with seams between adjacent inflatable members running vertically, approximating a line from the apical region of the heart to the basal region. The pattern of "banding" or arrangement of individual inflatable members in an assembly can be chosen to affect a desired pattern of force on the heart. If a given inflatable member is designed without a pressure point, i.e., has uniform contact with the epicardium after inflation, then the force across the contact surface for that inflatable member is expected to be relatively uniform. However, the force exerted by different inflatable members can be different, particularly if their contact profiles and/or fill pressures are different. Thus, by joining inflatable members in a given pattern, a desired force pattern can be applied to the heart. Further, in certain embodiments the pericardial reinforcement device can be individually tailored to match the size, shape, or pathology of the recipient heart. This can be accomplished, for example, by preparing a three-dimensional model of the patient's heart using CT scans or MRI, and then assembling precursor components, i.e., inflatable members of different size and shape, into a custom-fitted device. This can be done to assure optimum or uniform pressure application to the patient's heart as well as more stable placement and a better treatment outcome.

A method of designing a constraint device can include using individual patient heart data or averaged patient class data to construct a particular device configuration for a particular patient. This can involve determining the size and shape of an individual's heart, such as by collecting image data of the heart from one or more imaging modalities (e.g., ultrasound image, magnetic resonance image, x-ray or CT image, etc.) and using this data to select a particular constraint device configuration or to program the system controller to control separate inflatable regions to conform to the needs of a particular individual.

Figure 20:
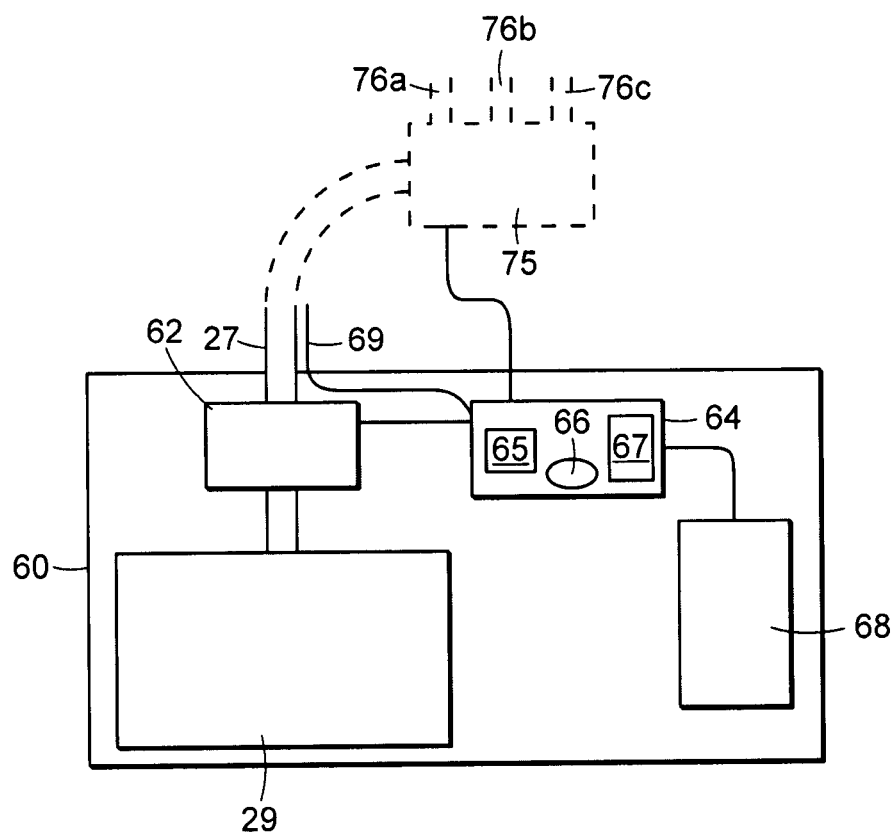
FIG. 20 depicts an embodiment of a control unit used to adjust the inward pressure of the pericardial reinforcement device against the heart.

For embodiments of the pericardial reinforcement device that employ adjustable confining pressure, it can be useful to surgically implant, e.g., in the abdomen, a control unit such as the one displayed in FIG. 20. A control unit either can be controlled from external instruments to adjust the confining pressure, or can be designed to automatically adjust the pressure without intervention. In control unit 60, fill line 27 from the pericardial reinforcement device is connected through pump 62 to fluid reservoir 29. Pump 62 is controlled by the components on circuit board 64, including processor 65, memory 67, and communication port 66. The electronic components are fed by battery 68. Lead 69 from one or more pressure sensors embedded within the inflatable members is connected to the circuit board and the processor. The communications port can contain a wireless transmitter and/or receiver to permit resetting pressure parameters or reprogramming from an external device and for the transmission of sensor or other stored data from the reinforcement device. An optional feature is manifold 75, which can be controlled by the processor to direct fluid flow to or from a selected inflatable section of the restraint device, using manifold outlet lines 76a, 76b, or 76c, each of which is connected to a separate inflatable member.

While the invention is described through the above-described exemplary embodiments, it will be understood by those of ordinary skill in the art that modifications to, and variations of, the illustrated embodiments may be made without departing from the inventive concepts disclosed herein. Accordingly, the invention should not be viewed as limited, except by the scope and spirit of the appended claims.

What is claimed:

1. A cardiac treatment device comprising:
a plurality of support elements that can be positioned in a pericardial space for placement about a surface of a mammalian heart;
an inflatable member that translates using the support elements from a first position within an insertion device to a deployed position within the pericardial space and surrounding the heart, the inflatable member having one or more inflatable chambers such that at least one inflatable chamber can receive a fluid under pressure;
a port to insert a fluid under pressure into at least one of the one or more inflatable chambers of the inflatable member;
an actuator of the insertion device that positions the inflatable member within the pericardial space; and
a plurality of rods that translate relative to the support elements, the rods being coupled to a distal end of the inflatable member such that movement of the rods within the pericardial space and relative to the support elements with the actuator operates to push the inflatable member to the deployed position that surrounds the heart within the pericardial space.

2. The device of claim 1 further comprising a pouch in fluid communication with the one or more inflatable chambers through a channel in the port for adjusting fluid pressure in the inflatable chamber.

3. The device of claim 1 wherein the inflatable member comprises separate sections attached to adjacent support elements.

4. The device of claim 1 wherein the inflatable chambers separately inflatable such that different confining pressures can be applied to different portions of an epicardial surface.

5. The device of claim 1 further comprising a sensor that measures fluid pressure in at least one inflatable chamber.

6. The device of claim 1 further comprising a plurality of sensors attached to the inflatable member.

7. The device of claim 1 further comprising one or more conductive elements attached to a surface of the inflatable member.

8. The device of claim 7 further comprising a controller electrically connected to the one or more conductive elements.

9. The device of claim 8 wherein the controller generates pacing signals delivered to myocardial tissue with the one or more conductive elements.

10. The device of claim 1 wherein a distal end of the inflatable member extends entirely around a circumference of the device.

11. The device of claim 1 wherein the first position comprises a folded configuration.

12. The device of claim 11 wherein the folded configuration comprises a plurality of folds extending circumferally about an axis.

13. The device of claim 1 wherein the cavity is positioned within the inflatable member such that a material can be inserted into the cavity to form a rigid outer wall.

14. The device of claim 1 wherein the plurality of rods are releasable from the inflatable member.

15. The device of claim 4 wherein the separately inflatable chambers have separate fluid ports.

16. The device of claim 1 further comprising a pump to control fluid pressure in the one or more inflatable chambers.

17. The device of claim 16 wherein the pump includes a manifold to select one or more of the inflatable chambers to adjust the fluid pressure in a section selected with the manifold.

18. The device of claim 16 wherein the pump is configured to pump fluid from a reservoir.

19. The device of claim 1 wherein the inflatable member comprises an implantable device that is fluidly coupled to a reservoir.

20. The device of claim 19 wherein the reservoir is adapted for implantation in an abdominal cavity with a control system.

21. The device of claim 20 wherein the reservoir and control system are within an implant housing, the implant housing having a communication device for percutaneous data transmission.

22. A minimally-invasive system for cardiac treatment comprising:
a percutaneous insertion device to insert an inflatable member into a mammalian pericardium pericardial space surrounding a heart, the insertion device including a handle and a first moving section that moves relative to the handle to actuate movement of an the inflatable member, the inflatable member coupled to at least one of the a plurality of support members and rod elements, the inflatable member having at least one inflatable chamber that is fillable with a fluid to at a selected pressure, such that the inflatable member can be deployed from a distal end of the percutaneous insertion device that is positioned adjacent to a heart apex;
an infusion port in fluid communication with the inflatable chamber;
a detachable rod for advancing plurality of coupler elements to detachably connect each rods element to the inflatable member such that movement of the rod elements relative to the insertion device is operative to position the inflatable member within a the pericardial space to surround a region of the heart; and
an actuator on the insertion device such that operation of the actuator moves the rod elements within the pericardial space that is external to the heart and translates the inflatable member to surround the heart during deployment within the pericardial space.

23. The system of claim 22 wherein the system further comprises a detaching mechanism that detaches a support member from the detachable rod.

24. The system of claim 22, the system further comprising a fluid delivery tube that is in fluid communication with the fluid infusion port for filling the inflatable chamber with a fluid.

25. The system of claim 23, the system further comprising a pouch for adjusting fluid pressure in the inflatable member after the detaching mechanism has detached the support member from the detachable rod.

26. The system of claim 22 wherein the inflatable member has separate sections that are disposed between adjacent support members.

27. The system of claim 26 wherein the separate sections of the inflatable chamber are separately inflatable chambers so that different confining pressures can be applied to different portions of the mammalian myocardium.

28. The system of claim 22 wherein the insertion device includes a second moving section that actuates movement of one or more support members through a distal opening of the insertion device.

29. The system of claim 22 wherein the insertion device comprises a splay element to direct an angle of insertion for a support member.

30. The system of claim 22 wherein the inflatable member is folded within the insertion device.

31. The system of claim 22 wherein the insertion device has a diameter for insertion through an intercostal space.

32. A method for using an insertion device to deploy an inflatable member, the method comprising:
inserting an insertion device into a mammalian pericardium through an intercostal space to a position adjacent an apex of a heart;
inserting a distal end of an inflatable member into a pericardial space with the insertion device, the insertion device attached to one or more detachable rod elements that are moveable in a distal direction from the insertion device;
using one or more of the detachable rod elements to translate the distal end of the inflatable member into the pericardial space such that the inflatable member moves to a position that surrounds the heart;
the one or more detachable rod elements from the inflatable member and removing said one or more detachable rod elements from the pericardial space; and
inserting a fluid into an inflatable chamber of the inflatable member within the pericardial space.

33. The method of claim 32 further comprising advancing the inflatable member by pulling mechanism on a pulley device or spindle that are disposed in each of a plurality of support members.

34. The method of claim 32 further comprising detaching the inflatable member having a plurality of support members from a plurality of the detachable rods.

35. The method of claim 34 further comprising adjusting fluid pressure in the inflatable chamber after detachment of the inflatable member from the one or more detachable rod elements.

36. The method of claim 34 further comprising positioning the inflatable member on a portion of the mammalian myocardium including positioning an inflatable member having a plurality of separately inflatable chambers.

37. The method of claim 32 further comprising programming a controller to selectively inflate the inflatable chamber within the inflatable member.

38. The method of claim 32 further comprising using patient heart data to program the controller to selectively inflate the inflatable chamber or a plurality of inflatable chambers.

39. The method of claim 32 further comprising inserting a plurality of support members into the pericardial space and inserting the inflatable member relative to the support members.

40. The method of claim 38 further comprising obtaining an image of the heart to provide patient heart data.

41. The method of claim 32 further comprising viewing insertion of the inflatable member using fluoroscopic guidance.

42. The method of claim 32 further comprising using a splaying mechanism to deploy the inflatable member.

43. The method of claim 42 further comprising splaying elements with the splaying mechanism mounted within the insertion device.

44. The method of claim 32 wherein the insertion device comprises a needle.

45. The method of claim 32 further comprising using a handle to position the one or more rod elements and pushing the one or more rod elements extending from a distal end of the insertion device into the pericardial cavity wherein the distal ends of the one or more rod elements are attached to the inflatable member.

46. The method of claim 32 further comprising inserting a distal end of the insertion device that comprises a tube having a plurality of the detachable rode elements and the inflatable member within the tube.

47. The method of claim 32 further comprising inserting a visualization device to generate images of the inflatable member during insertion.

* * * * *